(12) United States Patent
Wang et al.

(10) Patent No.: US 12,180,131 B2
(45) Date of Patent: Dec. 31, 2024

(54) ORGANIC MOLECULES FOR OPTOELECTRONIC DEVICES

(71) Applicant: SAMSUNG DISPLAY CO., LTD., Yongin-si (KR)

(72) Inventors: Qiang Wang, Karlsruhe (DE); Pascal Brandt, Bruchsal (DE)

(73) Assignee: Samsung Display Co., Ltd., Yongin-si (KR)

( * ) Notice: Subject to any disclaimer, the term of this patent is extended or adjusted under 35 U.S.C. 154(b) by 618 days.

(21) Appl. No.: 16/809,908

(22) Filed: Mar. 5, 2020

(65) Prior Publication Data
US 2020/0290941 A1 Sep. 17, 2020

(30) Foreign Application Priority Data

Mar. 13, 2019 (DE) ..................... 10 2019 106 388.4

(51) Int. Cl.
C07C 15/38 (2006.01)
C07C 205/06 (2006.01)
H10K 30/30 (2023.01)
H10K 50/11 (2023.01)
H10K 50/16 (2023.01)
H10K 85/60 (2023.01)

(52) U.S. Cl.
CPC ........... *C07C 15/38* (2013.01); *H10K 85/622* (2023.02); *C07C 205/06* (2013.01); *H10K 30/353* (2023.02); *H10K 50/11* (2023.02); *H10K 50/16* (2023.02)

(58) Field of Classification Search
CPC ..... C07C 15/38; C07C 205/06; C07C 211/50; C07C 211/61; C07C 255/51; C07C 255/52; C07C 255/58; C07C 2601/14; C07C 2603/24; C07C 2603/50; C07C 15/62; H01L 51/0054; H01L 51/4273; H01L 51/5012; H01L 51/5072; H01L 51/0052; H01L 51/0058; C07F 7/0805; Y02E 10/549; H10K 85/622; H10K 30/353; H10K 50/11; H10K 50/16; H10K 85/615; H10K 85/626
See application file for complete search history.

(56) References Cited

U.S. PATENT DOCUMENTS

2004/0076853 A1\* 4/2004 Jarikov ............... H01L 51/5012
428/917
2008/0105865 A1\* 5/2008 Oyamada ................ C07C 15/62
549/462

FOREIGN PATENT DOCUMENTS

| JP | 2006-117593 A | * | 5/2006 | | |
|---|---|---|---|---|---|
| JP | 2007-224171 A | * | 9/2007 | | |
| JP | 2008081704 A | * | 4/2008 | | |
| KR | 2012117675 A | * | 10/2012 | ......... | H01L 51/0054 |
| WO | WO-2006054426 A1 | * | 5/2006 | ............. | A61P 43/00 |
| WO | WO-2010137757 A1 | * | 12/2010 | ............. | C09K 11/06 |

OTHER PUBLICATIONS

Wang et al., ChemPhotoChem, (2018), vol. 2, pp. 749-756 (Year: 2018).\*
Kim et al., J. Org. Chem., (2008), vol. 73, pp. 5127-5130. (Year: 2008).\*
Chem. Rev., (2011), vol. 111, pp. 7260-7314. (Year: 2011).\*
Maeda, H., Maeda, T., Mizuno, K., Fujimoto, K., Shimizu, H., & Inouye, M. (2006). Alkynylpyrenes as improved pyrene-based biomolecular probes with the advantages of high fluorescence quantum yields and long absorption/emission wavelengths. Chemistry—A European Journal, 12(3), 824-831. (Year: 2006).\*
Hayer, A. et al., (2006). Highly fluorescent crystalline and liquid crystalline columnar phases of pyrene-based structures. The Journal of Physical Chemistry B, 110(15), 7653-7659. (Year: 2006).\*
Machine translation of KR-2012117675-A (publication date Oct. 2012). (Year: 2012).\*
Machine translation of JP-2008081704-A (publication date Apr. 2008) (Year: 2008).\*

(Continued)

*Primary Examiner* — Dawn L Garrett
(74) *Attorney, Agent, or Firm* — Lewis Roca Rothgerber Christie LLP

(57) ABSTRACT

An organic molecule having a structure of formula I:

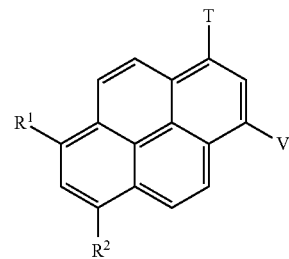

Formula I wherein
T and V is independently from another selected from the group consisting of $R^1$ and $R^2$; and
$R^1$ has a structure of formula II:

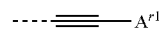

Formula II which is bonded via the position marked by the dotted line,
wherein $Ar^1$ is $C_6$-$C_{60}$-aryl.

20 Claims, No Drawings

(56) References Cited

OTHER PUBLICATIONS

Hu, Jian-yong, et al. "Synthesis and Photophysical Properties of Pyrene-Based Light-Emitting Monomers: Highly Pure-Blue-Fluorescent, Cruciform-Shaped Architectures." (2010): 72-79. (Year: 2010).*

Machine translation of WO 2010/137757 A1 (publication date: Dec. 2010). (Year: 2010).*

Ji, Shaomin, et al. "Tuning the intramolecular charge transfer of alkynylpyrenes: effect on photophysical properties and its application in design of Off-On fluorescent thiol probes." The Journal of Organic Chemistry 74.13 (2009): 4855-4865. (Year: 2009).*

Jagadish K. Salunke et al., "Pyrene based conjunction materials: synthesis, characterization and electroluminescent properties," Physical Chemistry Chemical Physics, Nov. 14, 2014, pp. 23320-23328, vol. 16, No. 42.

Samantha N. Keller et al., "A comparison of optical, electrochemical and self-assembling properties of two structural isomers based on 1,6- and 1,8-pyrenedione chromophores", New Journal of Chemistry, Feb. 21, 2018, pp. 2970-2978, vol. 42, No. 4.

Tohru Sato et al., "A light-emitting mechanism for organic light-emitting diodes: molecular design for inverted singlet-triplet structure and symmetry-controlled thermally activated delayed fluorescence", Journal of Material Chemistry C., Jan. 28, 2015, pp. 870-878, vol. 3, No. 4.

* cited by examiner

ORGANIC MOLECULES FOR OPTOELECTRONIC DEVICES

CROSS-REFERENCE TO RELATED APPLICATIONS

This application claims priority to German Patent Application No. 10 2019 106 388.4, filed Mar. 13, 2019, the disclosure of which is incorporated by reference herein in its entirety.

FIELD OF THE INVENTION

The invention relates to organic light-emitting molecules and their use in organic light-emitting diodes (OLEDs) and in other optoelectronic devices.

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The object of the present invention is to provide molecules which are suitable for use in optoelectronic devices.

This object is achieved by the invention which provides a new class of organic molecules.

According to the invention, the organic molecules are purely organic molecules, i.e. they do not contain any metal ions in contrast to metal complexes known for the use in optoelectronic devices. The organic molecules of the invention, however, include metalloids, in particular B, Si, Sn, Se, and/or Ge.

According to the present invention, the organic molecules exhibit emission maxima in the blue, sky-blue or green spectral range. The organic molecules exhibit in particular emission maxima between 420 nm and 520 nm, preferably between 440 nm and 495 nm, more preferably between 450 nm and 470 nm. The photoluminescence quantum yields of the organic molecules according to the invention are, in particular, 50% or more. The use of the molecules according to the invention in an optoelectronic device, for example, an organic light-emitting diode (OLED), leads to higher efficiencies or higher color purity, expressed by the full width at half maximum (FWHM) of emission, of the device. Corresponding OLEDs have a higher stability than OLEDs with known emitter materials and comparable color.

The organic light-emitting molecules according to the invention comprise or consist a structure of formula I:

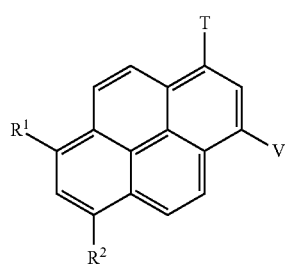

Formula I wherein
T and V is independently from another selected from the group consisting of $R^1$ and $R^2$;

$R^1$ is at each occurrence comprising or consisting of a structure of formula II:

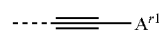

Formula II which is bonded to the structure shown above as Formula I via the position marked by the dotted line;

$Ar^1$ is $C_6$-$C_{60}$-aryl, which is optionally substituted with one or more substituents $R^6$;

$R^2$ is at each occurrence independently from another selected from the group consisting of OPh (Ph=phenyl), SPh, $CF_3$, CN, F, $Si(C_1$-$C_5$-alkyl$)_3$, $Si(Ph)_3$, $C_1$-$C_5$-alkyl,
  wherein optionally one or more hydrogen atoms are independently from each other substituted by deuterium, CN, $CF_3$, or F;

$C_1$-$C_5$-alkoxy,
  wherein optionally one or more hydrogen atoms are independently from each other substituted by deuterium, CN, $CF_3$, or F;

$C_1$-$C_5$-thioalkoxy,
  wherein optionally one or more hydrogen atoms are independently from each other substituted by deuterium, CN, $CF_3$, or F;

$C_2$-$C_5$-alkenyl,
  wherein optionally one or more hydrogen atoms are independently from each other substituted by deuterium, CN, $CF_3$, or F;

$C_2$-$C_5$-alkynyl,
  wherein optionally one or more hydrogen atoms are independently from each other substituted by deuterium, CN, $CF_3$, or F;

$C_6$-$C_{18}$-aryl,
  which is optionally substituted with one or more $C_1$-$C_5$-alkyl substituents;

$C_3$-$C_{17}$-heteroaryl,
  which is optionally substituted with one or more $C_1$-$C_5$-alkyl substituents;

$N(C_6$-$C_{18}$-aryl$)_2$,
$N(C_3$-$C_{17}$-heteroaryl$)_2$; and
$N(C_3$-$C_{17}$-heteroaryl)($C_6$-$C_{18}$-aryl);

$R^6$ is at each occurrence independently from another selected from the group consisting of hydrogen, deuterium, OPh, SPh, $CF_3$, CN, F, $Si(C_1$-$C_5$-alkyl$)_3$, $Si(Ph)_3$, $C_1$-$C_5$-alkyl,
  wherein optionally one or more hydrogen atoms are independently from each other substituted by deuterium, CN, $CF_3$, or F;

$C_1$-$C_5$-alkoxy,
  wherein optionally one or more hydrogen atoms are independently from each other substituted by deuterium, CN, $CF_3$, or F;

$C_1$-$C_5$-thioalkoxy,
  wherein optionally one or more hydrogen atoms are independently from each other substituted by deuterium, CN, $CF_3$, or F;

$C_2$-$C_5$-alkenyl,
  wherein optionally one or more hydrogen atoms are independently from each other substituted by deuterium, CN, $CF_3$, or F;

C$_2$-C$_5$-alkynyl,
wherein optionally one or more hydrogen atoms are independently from each other substituted by deuterium, CN, CF$_3$, or F;
C$_6$-C$_{18}$-aryl,
which is optionally substituted with one or more C$_1$-C$_5$-alkyl substituents;
C$_3$-C$_{17}$-heteroaryl,
which is optionally substituted with one or more C$_1$-C$_5$-alkyl substituents;
N(C$_6$-C$_{18}$-aryl)$_2$,
N(C$_3$-C$_{17}$-heteroaryl)$_2$; and
N(C$_3$-C$_{17}$-heteroaryl)(C$_6$-C$_{18}$-aryl).

According to the invention, exactly one (one and only one) moiety selected from the group consisting of T and V is R$^1$, and exactly one moiety selected from the group consisting of T and V is R$^2$.

In one embodiment of the organic molecules of the invention, Ar$^1$ is selected from the group consisting of:
Ph (phenyl), which is optionally substituted with one or more substituents independently from each other selected from the group consisting of Me, $^i$Pr, $^t$Bu, CN, CF$_3$, and Ph,
naphthyl, which is optionally substituted with one or more substituents independently from each other selected from the group consisting of Me, $^i$Pr, $^t$Bu, CN, CF$_3$, and Ph, and
anthracenyl, which is optionally substituted with one or more substituents independently from each other selected from the group consisting of Me, $^i$Pr, $^t$Bu, CN, CF$_3$, and Ph.

In one embodiment, R$^1$ is selected from the group consisting of:

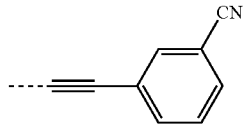

Formula IIa

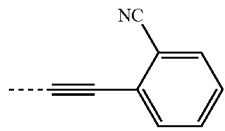

Formula IIb

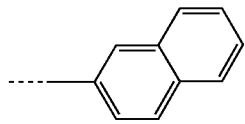

Formula IIc

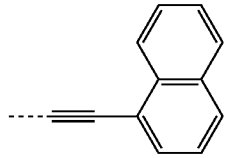

Formula IId

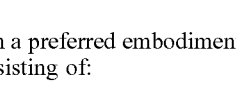

Formula IIe

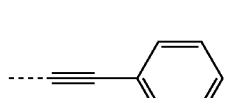

Formula IIf

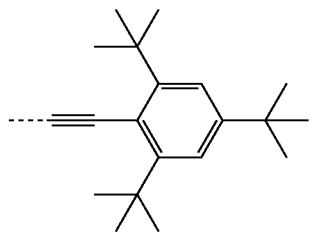

Formula IIg

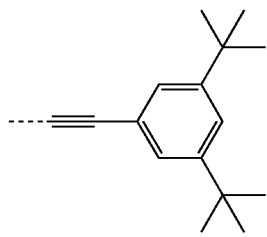

Formula IIh

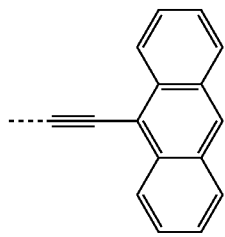

Formula IIi

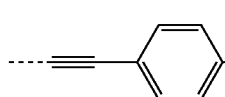

Formula IIj

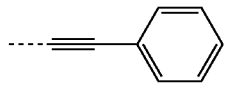

Formula IIk

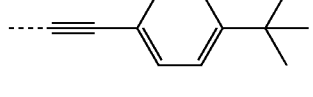

Formula IIm

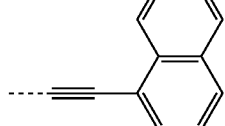

Formula IIn

In a preferred embodiment, R$^1$ is selected from the group consisting of:

Formula IIa

Formula IIb

-continued

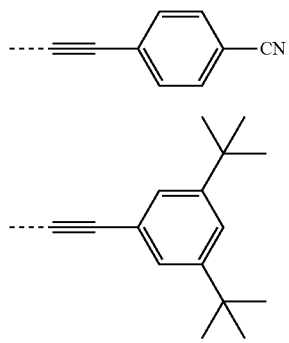

Formula IIc

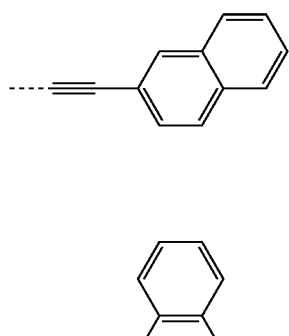

Formula IIh

Formula IIm

Formula IIn

In one embodiment, R² is selected from the group consisting of:

Me, ⁱPr, ᵗBu, SiMe₃, SiPh₃, and

Ph, which is optionally substituted with one or more substituents independently from each other selected from the group consisting of Me, ⁱPr, ᵗBu, and Ph.

In a preferred embodiment, R² is selected from the group consisting of:

ⁱPr, and

Ph, which is optionally substituted with one or more Ph substituents.

In one embodiment, the organic molecule comprises or consists of a structure of formula IIIa:

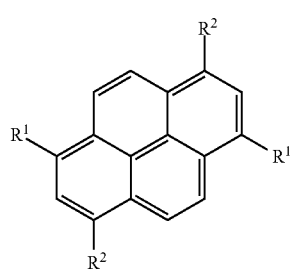

Formula IIIa wherein any one of the aforementioned definitions applies.

In one embodiment, the organic molecule comprises or consists of a structure of formula IIIb:

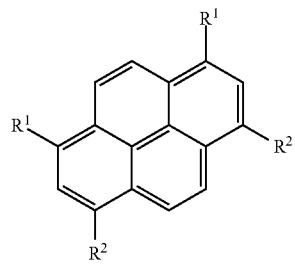

Formula IIIb wherein any one of the aforementioned definitions applies.

In one embodiment, the organic molecule comprises or consists of a structure selected from the group consisting of:

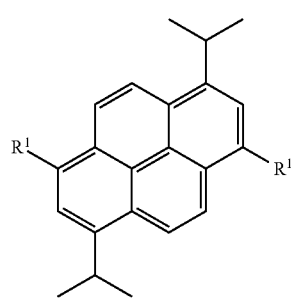

Formula IIIa-1

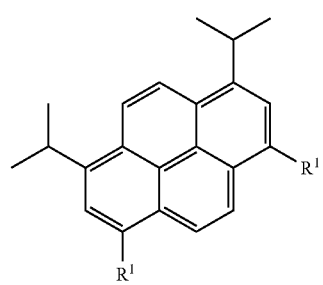

Formula IIIb-1

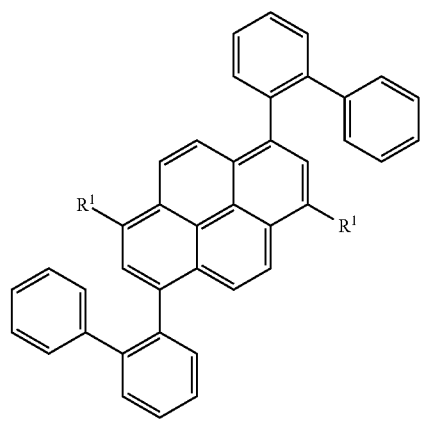

Formula IIIa-2

Formula IIIb-2

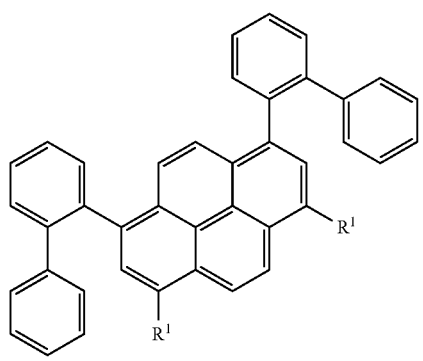

Formula IIIa-3

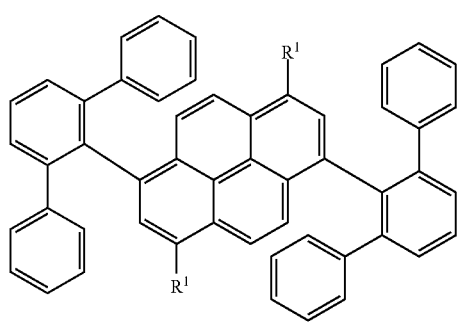

Formula IIIb-3

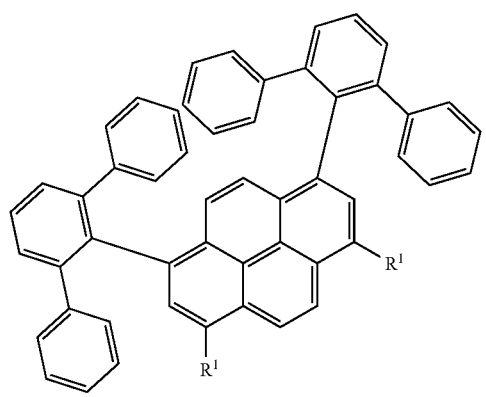

In a preferred embodiment, the organic molecule comprises or consists of a structure selected from the group consisting of Formula IIIa-1, Formula IIIb-1, Formula IIIa-2, Formula IIIb-2, Formula IIIa-3, and Formula IIIb-3, wherein $R^1$ is selected from the group consisting of:

Formula IIa

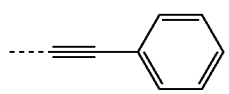

Formula IIb

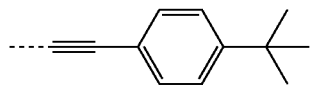

Formula IIc

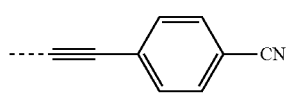

Formula IIh

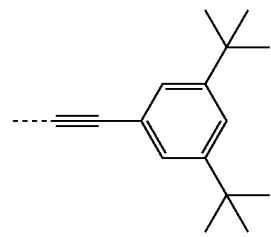

Formula IIm

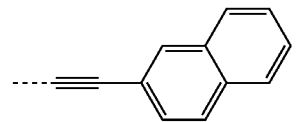

Formula IIn

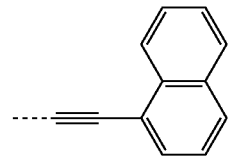

In one embodiment, the organic molecule comprises or consists of a structure selected from the group consisting of Formula IIIa-1, Formula IIIa-2, and Formula IIIa-3, wherein $R^1$ is selected from the group consisting of:

Formula IIa

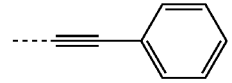

Formula IIb

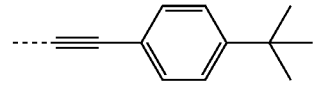

Formula IIc

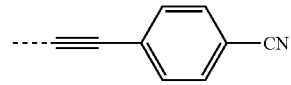

Formula IIh

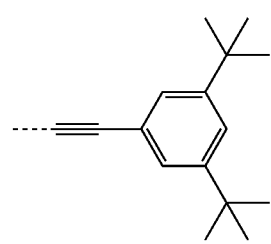

Formula IIm

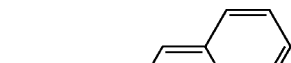

Formula IIn

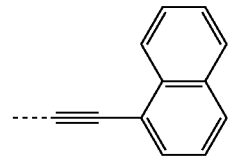

In one embodiment, the organic molecule comprises or consists of a structure selected from the group consisting of Formula IIIb-1, Formula IIIb-2, and Formula IIIb-3, wherein R¹ is selected from the group consisting of:

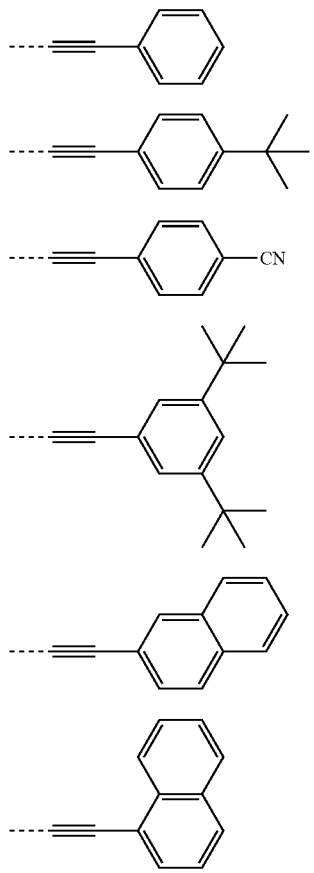

Formula IIa

Formula IIb

Formula IIc

Formula IIh

Formula IIm

Formula IIn

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used here throughout, the term "aryl group or heteroaryl group" comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout, the term "cyclic group" may be understood in the broadest sense as any mono-, bi- or polycyclic moieties.

As used throughout, the term "biphenyl" as a substituent may be understood in the broadest sense as ortho-biphenyl, meta-biphenyl, or para-biphenyl, wherein ortho, meta and para is defined in regard to the binding site to another chemical moiety.

As used throughout, the term "naphthyl" as a naphthalene substituent may be understood in the broadest sense as 1-naphthyl and 2-naphthyl, wherein "1-" and "2-" is defined in regard to the binding site to another chemical moiety, i.e.:

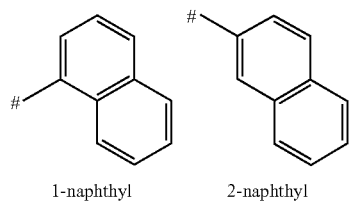

1-naphthyl     2-naphthyl wherein # indicates the binding site to another chemical moiety.

As used throughout, the term "anthracene" as a substituent may be understood in the broadest sense as 1-anthracenyl, 2-anthracenyl and 9-anthracenyl wherein "1-", "2-" and "9-" is defined in regard to the binding site to another chemical moiety, i.e.:

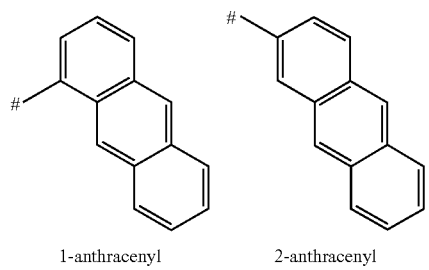

1-anthracenyl     2-anthracenyl

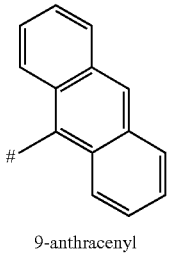

9-anthracenyl wherein # indicates the binding site to another chemical moiety.

As used throughout, the term "alkyl group" may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methyl-butyl, n-pentyl, s-pentyl, t-pentyl, 2-pentyl, neo-pentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl) octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout, the term "alkenyl" comprises linear, branched, and cyclic alkenyl substituents. The term "alkenyl group", for example, comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout, the term "alkynyl" comprises linear, branched, and cyclic alkynyl substituents. The term "alkynyl group", for example, comprises ethynyl, propynyl, butynyl, pentynyl, hexynyl, heptynyl or octynyl.

As used throughout, the term "alkoxy" comprises linear, branched, and cyclic alkoxy substituents. The term "alkoxy group" exemplarily comprises methoxy, ethoxy, n-propoxy, i-propoxy, n-butoxy, i-butoxy, s-butoxy, t-butoxy and 2-methylbutoxy.

As used throughout, the term "thioalkoxy" comprises linear, branched, and cyclic thioalkoxy substituents, in which the O of the exemplarily alkoxy groups is replaced by S.

As used throughout, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran).

As used herein, these different ways of designating a substituent or attached fragment are considered to be equivalent.

In one embodiment, the organic molecules according to the invention have an excited state lifetime of not more than 150 µs, of not more than 100 µs, in particular of not more than 50 µs, more preferably of not more than 10 µs or not more than 7 µs in a film of poly(methyl methacrylate) (PMMA) with 5% by weight of organic molecule at room temperature.

In a further embodiment of the invention, the organic molecules according to the invention have an emission peak in the visible or nearest ultraviolet range, i.e., in the range of a wavelength of from 380 nm to 800 nm, with a full width at half maximum of less than 0.23 eV, preferably less than 0.20 eV, more preferably less than 0.19 eV, even more preferably less than 0.18 eV or even less than 0.17 eV in a film of poly(methyl methacrylate) (PMMA) with 5% by weight of organic molecule at room temperature.

Orbital and excited state energies can be determined either by means of experimental methods. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly (methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross. For the organic molecules according to the invention, $E^{gap}$ is determined as the energy at which the excitation and emission spectra of a film with 0.1 mg/mL in DCM of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated, measured in a film of PMMA with 10% by weight of emitter and in case of the organic molecules according to the invention with 0.1 mg/mL in DCM of the organic molecules according to the invention. Both for host and emitter compounds, the energy of the first excited singlet state S1 is determined from the onset of the emission spectrum, if not otherwise stated, measured in a film of PMMA with 10% by weight of host or emitter compound and in case of the organic molecules according to the invention with 0.1 mg/mL in DCM of the organic molecules according to the invention.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

In one embodiment, the organic molecules according to the invention have an onset of the emission spectrum, which is energetically close to the emission maximum, i.e. the energy difference between the onset of the emission spectrum and the energy of the emission maximum is below 0.14 eV, preferably below 0.13 eV, or even below 0.12 eV, while the full width at half maximum (FWHM) of the organic molecules is less than 0.23 eV, preferably less than 0.20 eV, more preferably less than 0.19 eV, even more preferably less than 0.18 eV or even less than 0.17 eV with 0.1 mg/mL in DCM of organic molecule at room temperature, resulting in a CIEy coordinate below 0.20, preferably below 0.18, more preferably below 0.16 or even more preferred below 0.14.

A further aspect of the invention relates to the use of an organic molecule of the invention as a luminescent emitter or as an absorber, and/or as a host material and/or as an electron transport material, and/or as a hole injection material, and/or as a hole blocking material in an optoelectronic device.

A preferred embodiment relates to the use of an organic molecule according to the invention as a luminescent emitter in an optoelectronic device.

The optoelectronic device may be understood in the broadest sense as any device based on organic materials that is suitable for emitting light in the visible or nearest ultraviolet (UV) range, i.e. in the range of a wavelength of from 380 to 800 nm. More preferably, the optoelectronic device may be able to emit light in the visible range, i.e. light of from 400 nm to 800 nm.

In the context of such use, the optoelectronic device is more particularly selected from the group consisting of:
  organic light-emitting diodes (OLEDs),
  light-emitting electrochemical cells,
  OLED sensors, especially in gas and vapor sensors that are not hermetically shielded to the surroundings,
  organic diodes,
  organic solar cells,
  organic transistors,
  organic field-effect transistors,
  organic lasers, and
  down-conversion elements.

In a preferred embodiment in the context of such use, the optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an optoelectronic device, more particularly in an OLED, is 0.1% to 99% by weight, more particularly 1% to 80% by weight. In an alternative embodiment, the proportion of the organic molecule in the emission layer is 100% by weight.

In one embodiment, the light-emitting layer comprises not only the organic molecules according to the invention, but also a host material whose triplet (T1) and singlet (S1) energy levels are energetically higher than the triplet (T1) and singlet (S1) energy levels of the organic molecule.

A further aspect of the invention relates to a composition comprising or consisting of:
  (a) at least one organic molecule according to the invention, in particular in the form of an emitter and/or a host, and
  (b) one or more emitter and/or host materials, which differ from the organic molecule according to the invention and
  (c) optional one or more dyes and/or one or more solvents.

In one embodiment, the light-emitting layer comprises (or essentially consists of) a composition comprising or consisting of:

(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

In a particular embodiment, the light-emitting layer EML comprises (or essentially consists of) a composition comprising or consisting of:
  (i) 0.1-10% by weight, preferably 0.5-5% by weight, in particular 1-3% by weight, of one or more organic molecules according to the invention;
  (ii) 5-99% by weight, preferably 15-85% by weight, in particular 20-75% by weight, of at least one host compound H; and
  (iii) 0.9-94.9% by weight, preferably 14.5-80% by weight, in particular 24-77% by weight, of at least one further host compound D with a structure differing from the structure of the molecules according to the invention; and
  (iv) optionally 0-94% by weight, preferably 0-65% by weight, in particular 0-50% by weight, of a solvent; and
  (v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention, in particular transferred from the first excited triplet state T1(H) of the host compound H to the first excited triplet state T1(E) of the one or more organic molecules according to the invention E and/or from the first excited singlet state S1(H) of the host compound H to the first excited singlet state S1(E) of the one or more organic molecules according to the invention E.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H) > E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and
  the at least one further host compound D has a highest occupied molecular orbital HOMO(D) having an energy $E^{HOMO}(D)$ and a lowest unoccupied molecular orbital LUMO(D) having an energy $E^{LUMO}(D)$,
  the organic molecule according to the invention E has a highest occupied molecular orbital HOMO(E) having an energy $E^{HOMO}(E)$ and a lowest unoccupied molecular orbital LUMO(E) having an energy $E^{LUMO}(E)$,
wherein
  $E^{HOMO}(H) > E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}$(H)) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}$(H)>$E^{LUMO}$(D) and the difference between the energy level of the lowest unoccupied molecular orbital LUMO(E) of the organic molecule according to the invention E ($E^{LUMO}$(E)) and the lowest unoccupied molecular orbital LUMO(D) of the at least one further host compound D ($E^{LUMO}$(D)) is between −0.5 eV and 0.5 eV, more preferably between −0.3 eV and 0.3 eV, even more preferably between −0.2 eV and 0.2 eV or even between −0.1 eV and 0.1 eV.

In one embodiment of the invention the host compound D and/or the host compound H is a thermally-activated delayed fluorescence (TADF)-material. TADF materials exhibit a $\Delta E_{ST}$ value, which corresponds to the energy difference between the first excited singlet state (S1) and the first excited triplet state (T1), of less than 2500 cm$^{-1}$. Preferably the TADF material exhibits a $\Delta E_{ST}$ value of less than 3000 cm$^{-1}$, more preferably less than 1500 cm$^{-1}$, even more preferably less than 1000 cm$^{-1}$ or even less than 500 cm$^{-1}$.

In one embodiment, the host compound D is a TADF material and the host compound H exhibits a $\Delta E_{ST}$ value of more than 2500 cm$^{-1}$. In a particular embodiment, the host compound D is a TADF material and the host compound H is selected from group consisting of CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl) phenyl]-9H-carbazole and 9-[3,5-bis(2-dibenzothiophenyl) phenyl]-9H-carbazole.

In one embodiment, the host compound H is a TADF material and the host compound D exhibits a $\Delta E_{ST}$ value of more than 2500 cm$^{-1}$. In a particular embodiment, the host compound H is a TADF material and the host compound D is selected from group consisting of T2T (2,4,6-tris(biphenyl-3-yl)-1,3,5-triazine), T3T (2,4,6-tris(triphenyl-3-yl)-1,3, 5-triazine) and/or TST (2,4,6-tris(9,9'-spirobifluorene-2-yl)-1,3,5-triazine).

In a further aspect, the invention relates to an optoelectronic device comprising an organic molecule or a composition of the type described here, more particularly in the form of a device selected from the group consisting of organic light-emitting diode (OLED), light-emitting electrochemical cell, OLED sensor (particularly gas and vapor sensors not hermetically externally shielded), organic diode, organic solar cell, organic transistor, organic field-effect transistor, organic laser and down-conversion element.

In a preferred embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention E is used as emission material in a light-emitting layer EML.

In one embodiment of the optoelectronic device of the invention, the light-emitting layer EML consists of the composition according to the invention described here.

When the optoelectronic device is an OLED, it may, for example, have the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, wherein the OLED comprises each layer selected from the group of HIL, HTL, EBL, HBL, ETL, and EIL only optionally, different layers may be merged and the OLED may comprise more than one layer of each layer type defined above.

Furthermore, the optoelectronic device may, in one embodiment, comprise one or more protective layers protecting the device from damaging exposure to harmful species in the environment including, for example, moisture, vapor and/or gases.

In one embodiment of the invention, the optoelectronic device is an OLED, with the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A wherein the OLED comprises each layer selected from the group of HIL, HTL, EBL, HBL, ETL, and EIL only optionally, different layers may be merged and the OLED may comprise more than one layer of each layer types defined above.

In one embodiment of the invention, the optoelectronic device is an OLED, which may have a stacked architecture. In this architecture, contrary to the typical arrangement in which the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow for a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may, for example, comprise indium tin oxide, aluminum zinc oxide, fluorine doped tin oxide, indium zinc oxide, PbO, SnO, zirconium oxide, molybdenum oxide, vanadium oxide, tungsten oxide, graphite, doped Si, doped Ge, doped GaAs, doped polyaniline, doped polypyrrol and/or doped polythiophene.

The anode layer A (essentially) may consist of indium tin oxide (ITO) (e.g., $(InO_3)_{0.9}(SnO_2)_{0.1}$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may, for example, comprise PEDOT:PSS (poly-3,4-ethylendioxy thiophene: polystyrene sulfonate), PEDOT (poly-3,4-ethylendioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenylamino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL), a hole transport layer (HTL) is typically located. Herein, any hole transport compound may be used. For example, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. For example, the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenylamine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may, for example, be used as inorganic dopant. Tetrafluorotetracyanoquinodimethane ($F_4$-TCNQ), copper-pentafluorobenzoate (Cu(I)pFBz) or transition metal complexes may, for example, be used as organic dopant.

The EBL may, for example, comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), the light-emitting layer EML is typically located. The light-emitting layer EML comprises at least one light emitting molecule. Particularly, the EML comprises at least one light emitting molecule according to the invention E. In one embodiment, the light-emitting layer comprises only the organic molecules according to the invention. Typically, the EML additionally comprises one or more host materials H. For example, the host material H is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl]ether oxide), 9-[3-(dibenzofuran-2-yl) phenyl]-9H-carbazole, 9-[3-(dibenzofuran-2-yhphenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting organic molecule according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl) phenyl]-9H-carbazole and 9-[3,5-bis(2-dibenzothiophenyl) phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML, an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl).

Optionally, the ETL may be doped with materials such as

Liq. The electron transport layer (ETL) may also block holes or a holeblocking layer (HBL) is introduced. The HBL may, for example, comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl) benzene).

Adjacent to the electron transport layer (ETL), a cathode layer C may be located. The cathode layer C may, for example, comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) intransparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, the electron transport layer (ETL) and/or a hole blocking layer (HBL) may also comprise one or more host compounds H.

In order to modify the emission spectrum and/or the absorption spectrum of the light-emitting layer EML further, the light-emitting layer EML may further comprise one or more further emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the organic emitter molecule according to the invention to the emitter molecule F before relaxing to the ground state SO by emitting light typically red-shifted in comparison to the light emitted by an organic molecule. Optionally, the emitter molecule F may also provoke two-photon effects (i.e., the absorption of two photons of half the energy of the absorption maximum).

Optionally, an optoelectronic device (e.g., an OLED) may, for example, be an essentially white optoelectronic device. For example, such white optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
 violet: wavelength range of >380-420 nm;
 deep blue: wavelength range of >420-480 nm;
 sky blue: wavelength range of >480-500 nm;
 green: wavelength range of >500-560 nm;
 yellow: wavelength range of >560-580 nm;
 orange: wavelength range of >580-620 nm;
 red: wavelength range of >620-800 nm.

With respect to emitter molecules, such colors refer to the emission maximum. Therefore, for example, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

Accordingly, a further aspect of the present invention relates to an OLED, which exhibits an external quantum efficiency at 1000 $cd/m^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 $cd/m^2$ of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.30 eV, preferably less than 0.25 eV, more preferably less than 0.20 eV, even more preferably less than 0.19 eV or even less than 0.17 eV.

A further aspect of the present invention relates to an OLED, which emits light with CIEx and CIEy color coordinates close to the CIEx(=0.131) and CIEy(=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The optoelectronic device, in particular the OLED according to the present invention can be fabricated by any means of vapor deposition and/or liquid processing. Accordingly, at least one layer is
 prepared by means of a sublimation process,
 prepared by means of an organic vapor phase deposition process,
 prepared by means of a carrier gas sublimation process,
 solution processed or printed.

The methods used to fabricate the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes, for example, comprise thermal (co)evaporation, chemical vapor deposition and physical vapor deposition. For active matrix OLED display, an AMOLED backplane is used as substrate. The individual layer may be processed from solutions or dispersions employing adequate solvents. Solution deposition process, for example, comprise spin coating, dip coating and jet printing. Liquid processing may optionally be carried out in an inert atmosphere (e.g., in a nitrogen atmosphere) and the solvent may be completely or partially removed by means known in the state of the art.

EXAMPLES

General Synthesis Scheme I

General synthesis scheme I provides a synthesis scheme for organic molecules according to the invention wherein $T=R^2$ and $V=R^1$:

General Procedure for Synthesis AA V1:

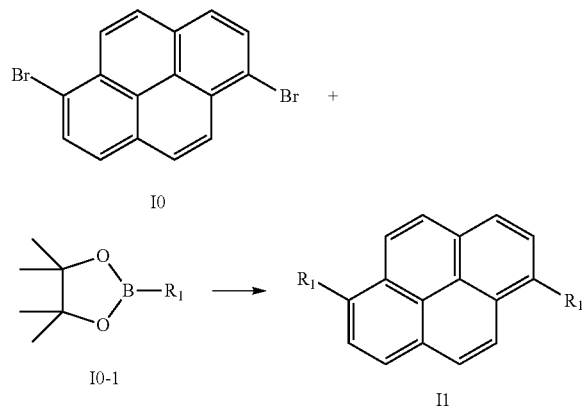

I0 (1.00 equivalents), I0-1 (2.20 equivalents), tetrakis(triphenylphosphine)palladium(0) Pd(PPh$_3$)$_4$ (0.04 equivalents; CAS: 14221-01-3), and potassium carbonate (K$_2$CO$_3$; 4.00 equivalents) are stirred under nitrogen atmosphere in dioxane:water (4:1 volume ratio) at 110° C. overnight. After cooling down to room temperature (rt) the reaction mixture is extracted between DCM and brine and the phases are separated. The combined organic layers are dried over MgSO$_4$ and then the solvent is removed under reduced pressure. The crude product obtained is purified by recrystallization or column chromatography and AAV1 is obtained as solid. Instead of a boronic acid ester, a corresponding boronic acid may be used.

General Procedure for Synthesis AA V2:

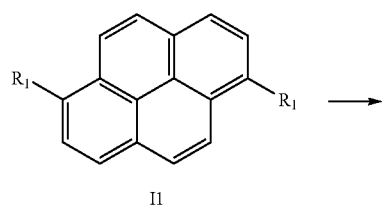

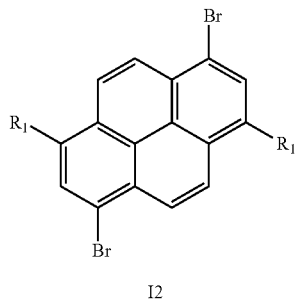

I1 (1.00 equivalents) and liquid bromine (4.0 equivalents; CAS 7726-95-6) are stirred under nitrogen atmosphere in anhydrous dimethylformamide (DMF) at room temperature (RT) overnight. The reaction mixture is poured into water. The precipitates are filtered off, washed with water and ethanol. The crude product obtained is purified by recrystallization or column chromatography and AAV2 is obtained as solid.

General Procedure for Synthesis AA V3:

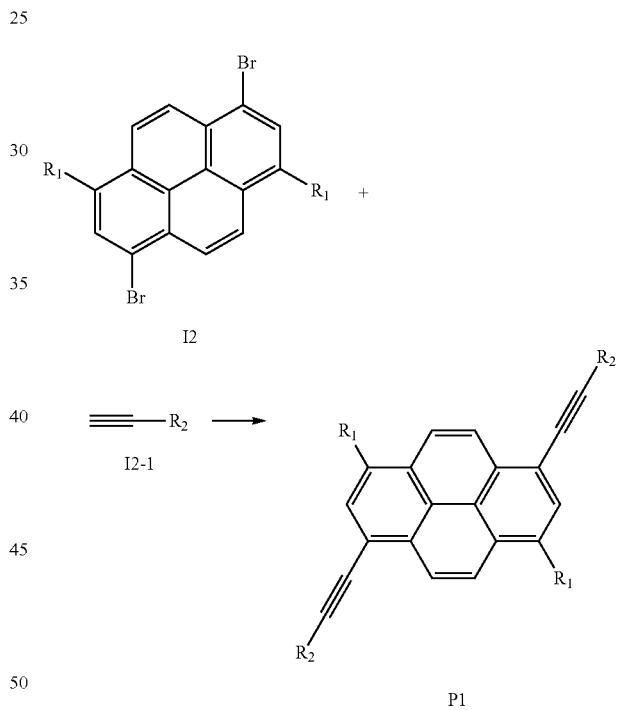

I2 (1.00 equivalents), I2-1 (2.20 equivalents), bis(triphenylphosphine)palladium(II)dichloride PdCl$_2$(PPh$_3$)$_2$ (0.04 equivalents; CAS 13965-03-2), copper(I)iodide (0.04 equivalents; CAS 7681-65-4) and triphenylphosphine (0.08 equivalents; CAS 603-35-0) are dissolved in triethylamine (Et$_3$N) and tetrahydrofuran (THF)mixed solvent (1:3 volumn ratio) under nitrogen atmosphere and the solution stirred at 70° C. overnight. After cooling down to room temperature (rt) the reaction mixture is extracted between DCM and brine and the phases are separated. The combined organic layers are dried over MgSO$_4$ and then the solvent is removed under reduced pressure. The crude product obtained is purified by recrystallization or column chromatography.

General Synthesis Scheme II

General synthesis scheme II provides a synthesis scheme for the organic molecules of the invention, wherein $T=R^1$ and $V=R^2$:

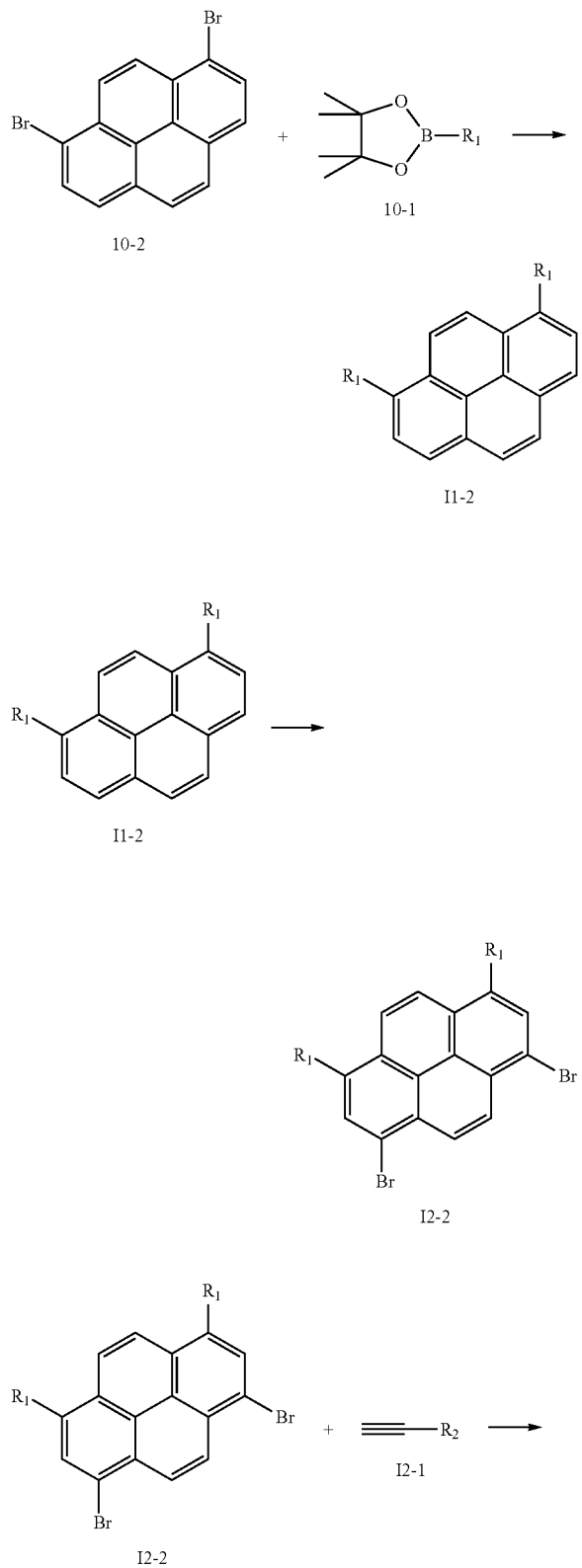

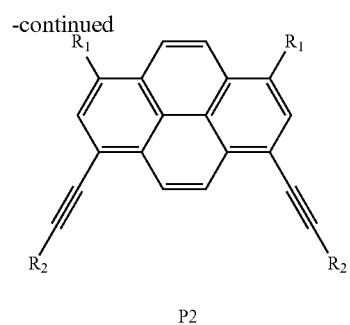

The individual reaction steps are performed under similar conditions as described in General scheme I for AAV1, AAV2, and AAV3.

Cyclic Voltammetry

Cyclic voltammograms are measured from solutions having concentration of $10^{-3}$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using $FeCp_2/FeCp_2^+$ as internal standard. The HOMO data was corrected using ferrocene as internal standard against a saturated calomel electrode (SCE).

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence spectroscopy and time-correlated single-photon counting (TCSPC) Steady-state emission spectroscopy is measured by a Horiba Scientific, Modell FluoroMax-4 equipped with a 150 W Xenon-Arc lamp, excitation and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation sources:

NanoLED 370 (wavelength: 371 nm, puls duration: 1,1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Time-resolved PL spectroscopy in the μs-range (FS5)

Time-resolved PL measurements were performed on a FS5 fluorescence spectrometer from Edinburgh Instruments. Compared to measurements on the HORIBA setup, better light gathering allows for an optimized signal to noise ratio, which favors the FS5 system especially for transient PL measurements of delayed fluorescence characteristics. The FS5 consists of a xenon lamp providing a broad spectrum. The continuous light source is a 150W xenon arc lamp, selected wavelengths are chosen by a Czerny-Turner monochromator, which is also used to set specific emission wavelengths. The sample emission is directed towards a sensitive R928P photomultiplier tube (PMT), allowing the detection of single photons with a peak quantum efficiency of up to 25% in the spectral range between 200 nm to 870 nm. The detector is a temperature stabilized PMT, providing dark counts below 300 cps (counts per second). Finally, to determine the transient decay lifetime of the delayed fluorescence, a tail fit using three exponential functions is applied. By weighting the specific lifetimes $\tau_i$ with their corresponding amplitudes $A_i$, $$\tau_{DF} = \sum_{i=1}^{3} \frac{A_i \tau_i}{A_i}$$

the delayed fluorescence lifetime $\tau_{DF}$ is determined.

Photoluminescence quantum yield measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields ϕ in % and CIE coordinates as x,y values. PLQY is determined using the following protocol:
1) Quality assurance: Anthracene in ethanol (known concentration) is used as reference
2) Excitation wavelength: the absorption maximum of the organic molecule is determined and the molecule is excited using this wavelength
3) Measurement Quantum yields are measured, for sample, of solutions or films under nitrogen atmosphere. The yield is calculated using the equation:

$$\Phi_{PL} = \frac{n_{photon}, \text{emitted}}{n_{photon}, \text{absorbed}} = \frac{\int \frac{\lambda}{hc} [Int_{emitted}^{sample}(\lambda) - Int_{absorbed}^{sample}(\lambda)] d\lambda}{\int \frac{\lambda}{hc} [Int_{emitted}^{reference}(\lambda) - Int_{absorbed}^{reference}(\lambda)] d\lambda}$$

wherein $n_{photon}$ denotes the photon count and Int. the intensity.

Production and Characterization of Optoelectronic Devices

Optoelectronic devices, such as OLED devices, comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc. Accelerated lifetime measurements are performed (e.g. applying increased current densities). For example, LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given.

HPLC-MS

HPLC-MS analysis is performed on an HPLC by Agilent (1100 series) with MS-detector (Thermo LTQ XL).

For example, a typical HPLC method is as follows: a reverse phase column 4.6 mm×150 mm, particle size 3.5 μm from Agilent (ZORBAX Eclipse Plus 95ø C18, 4.6×150 mm, 3.5 μm HPLC column) is used in the HPLC. The HPLC-MS measurements are performed at room temperature (rt) following gradients

| Flow rate [ml/min] | Time [min] | A [%] | B [%] | C [%] |
|---|---|---|---|---|
| 2.5 | 0 | 40 | 50 | 10 |
| 2.5 | 5 | 40 | 50 | 10 |
| 2.5 | 25 | 10 | 20 | 70 |
| 2.5 | 35 | 10 | 20 | 70 |
| 2.5 | 35.01 | 40 | 50 | 10 |
| 2.5 | 40.01 | 40 | 50 | 10 |
| 2.5 | 41.01 | 40 | 50 | 10 | using the following solvent mixtures:

| Solvent A: | $H_2O$ (90%) | MeCN (10%) |
| Solvent B: | $H_2O$ (10%) | MeCN (90%) |
| Solvent C: | THF (50%) | MeCN (50%) |

An injection volume of 5 μL from a solution with a concentration of 0.5 mg/mL of the analyte is taken for the measurements.

Ionization of the probe is performed using an atmospheric pressure chemical ionization (APCI) source either in positive (APCI+) or negative (APCI−) ionization mode.

Example 1

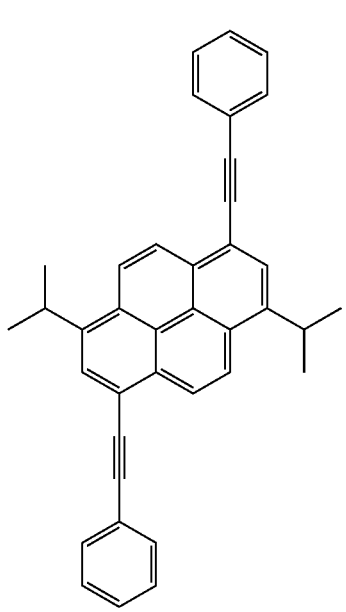 [SMILES: CC(C)c1cc(C#Cc2ccccc2)c2ccc3c(C(C)C)cc(C#Cc4ccccc4)c4ccc1c2c43]

Example 1 was synthesized according to General synthesis scheme I and according to AAV3 (54% yield), wherein

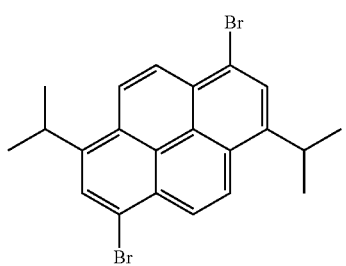 [SMILES: CC(C)c1cc(Br)c2ccc3c(C(C)C)cc(Br)c4ccc1c2c43]

(CAS 869340-02-3) was used as reactant I2.

MS (HPLC-MS), m/z (retention time): 487.25 (13.28 min).

The emission maximum of example 1 (0.1 mg/mL in dichloromethane (DCM)) is at 440 nm (2.82 eV), the full width at half maximum (FWHM) is 0.24 eV and the CIEy coordinate is 0.08. The onset of the emission spectrum is determined at 2.89 eV.

Example 1

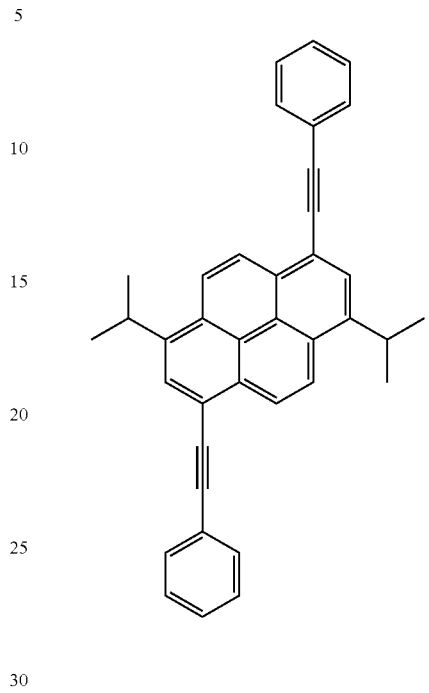

Example 1 was synthesized according to General synthesis scheme I and according to AAV3 (54% yield), wherein

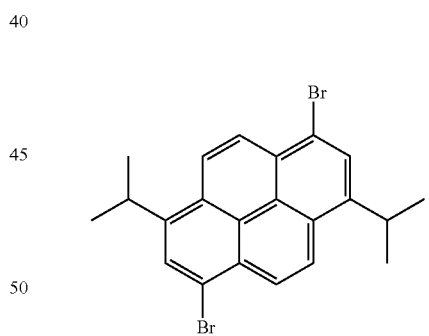

(CAS 869340-02-3) was used as reactant I2.

MS (HPLC-MS), m/z (retention time): 487.25 (13.28 min).

The emission maximum of example 1 (0.1 mg/mL in dichloromethane (DCM)) is at 440 nm (2.82 eV), the full width at half maximum (FWHM) is 0.24 eV and the CIEy coordinate is 0.08. The onset of the emission spectrum is determined at 2.89 eV.

Example 2

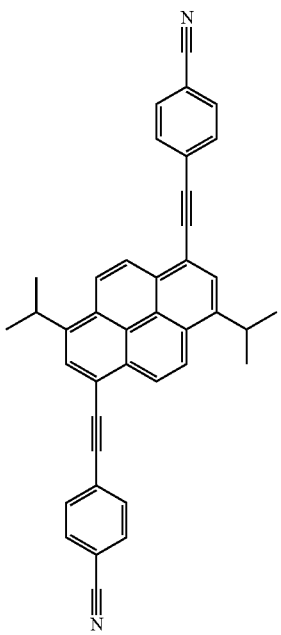 [SMILES: CC(C)c1cc(C#Cc2ccc(C#N)cc2)c2ccc3c(C(C)C)cc(C#Cc4ccc(C#N)cc4)c4ccc1c2c43]

Example 3

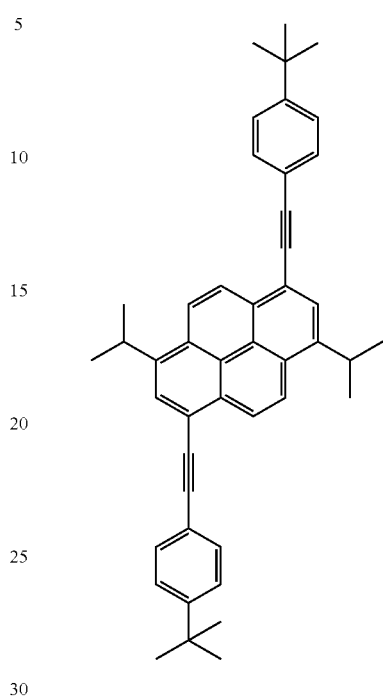

Example 2 was synthesized according to General synthesis scheme I and according to AAV3 (19% yield), wherein Example 3 was synthesized according to General synthesis scheme I and according to AAV3 (87% yield), wherein

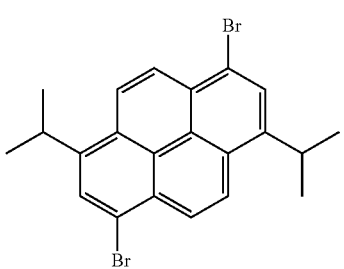 [SMILES: CC(C)c1cc(Br)c2ccc3c(C(C)C)cc(Br)c4ccc1c2c43]

(CAS 869340-02-3) was used as reactant I2.

MS (HPLC-MS), m/z (retention time): 536.34 (14.20 min).

The emission maximum of example 2 (0.001 mg/mL in dichloromethane (DCM)) is at 463 nm (2.68 eV) and the CIEy coordinate is 0.23. The onset of the emission spectrum is determined at 2.77 eV.

(CAS 869340-02-3) was used as reactant I2.

MS (HPLC-MS), m/z (retention time): 597.40 (15.35 min).

The emission maximum of example 3 (0.001 mg/mL in dichloromethane (DCM)) is at 443 nm (2.80 eV), the full width at half maximum (FWHM) is 0.24 eV and the CIEy coordinate is 0.10. The onset of the emission spectrum is determined at 2.88 eV.

Additional Examples of Organic Molecules of the Invention
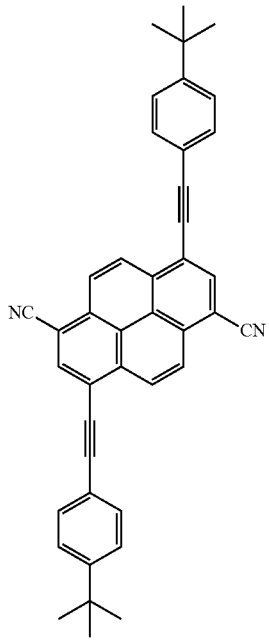
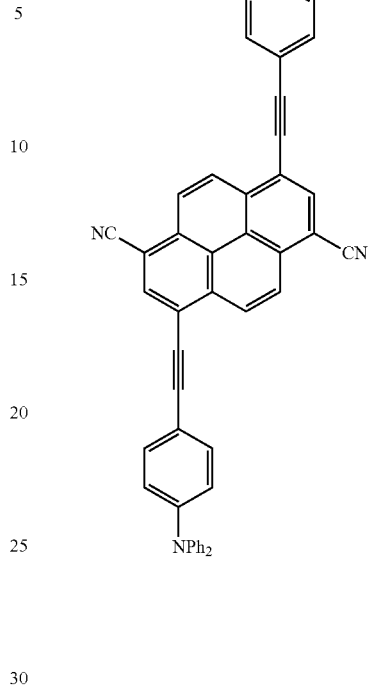
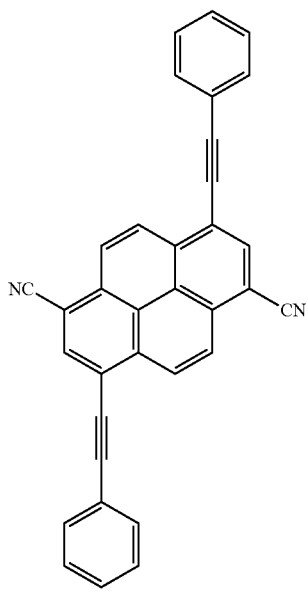
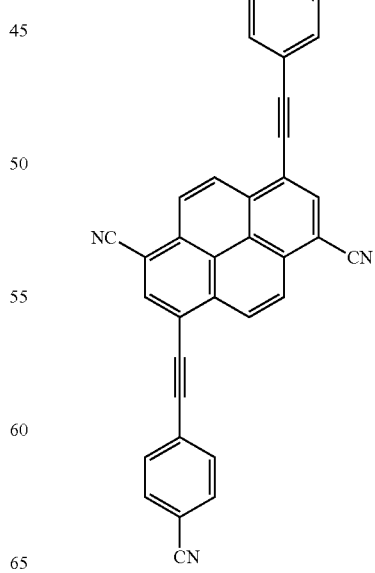

33
-continued
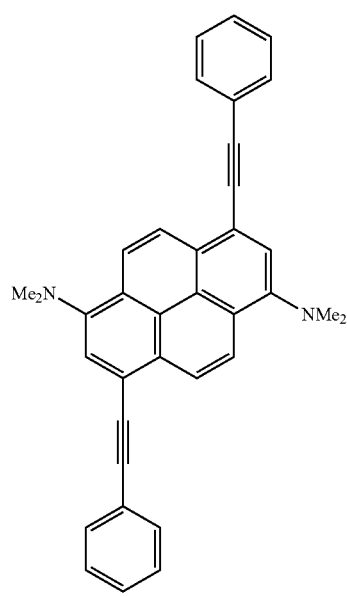
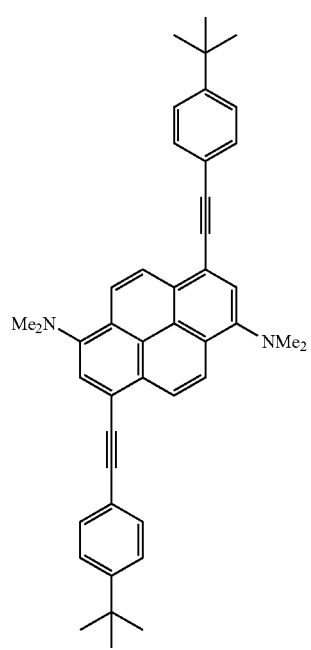
34
-continued
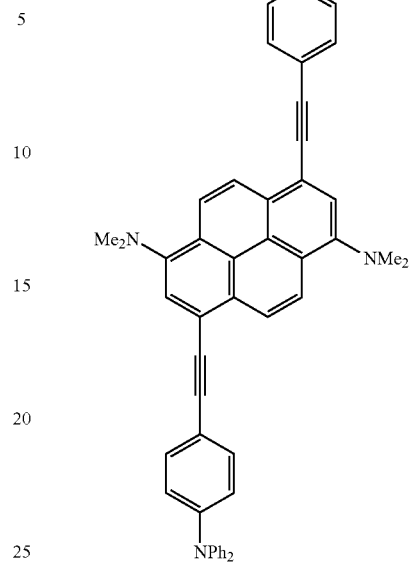
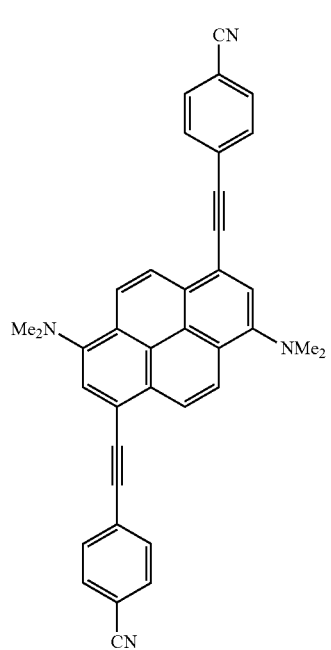

35
-continued
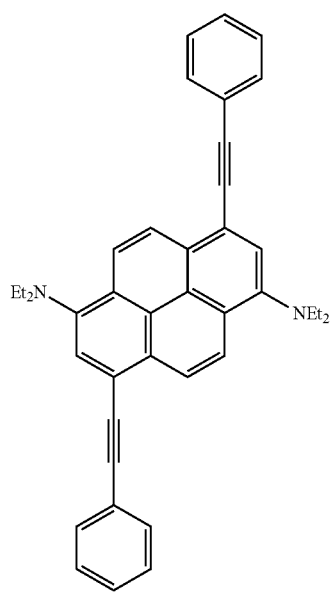
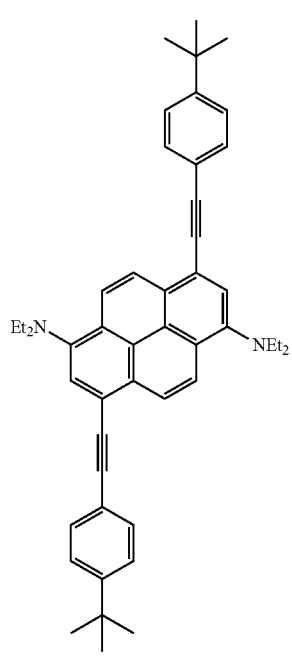
36
-continued
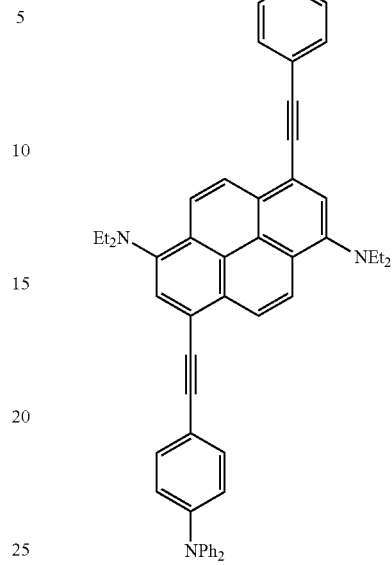
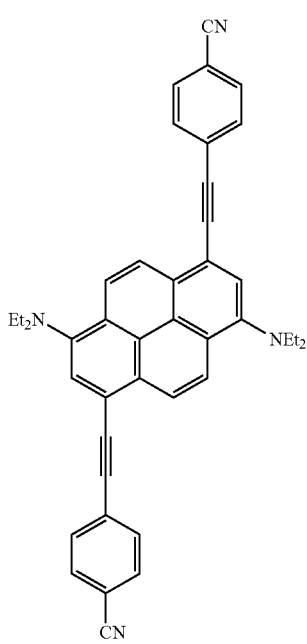

37
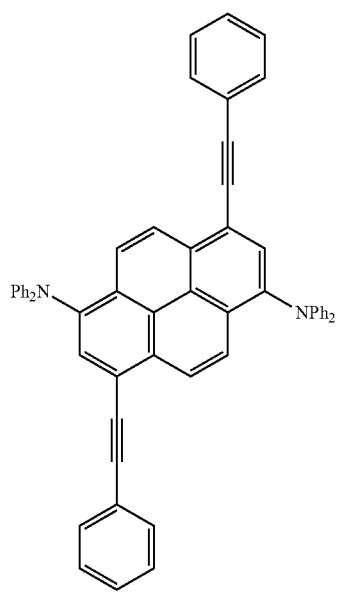
38
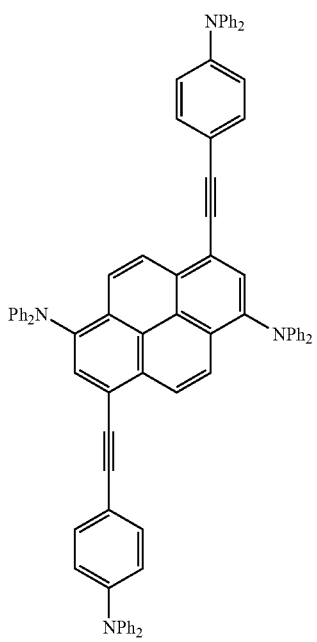
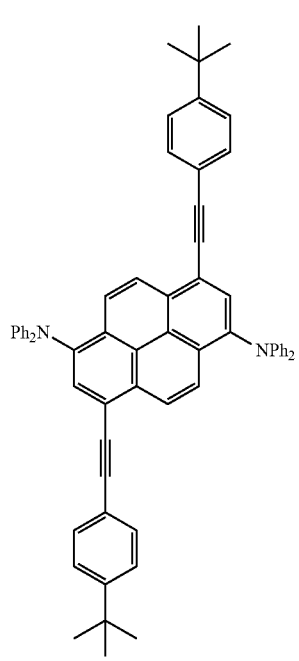
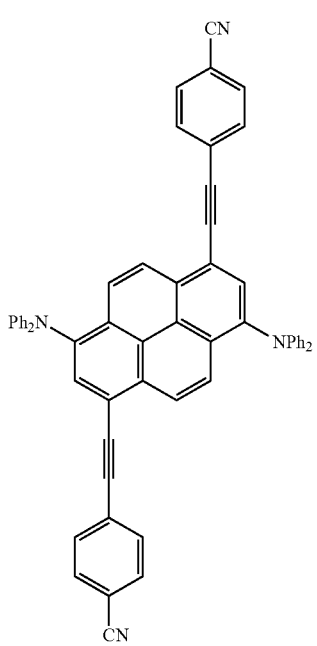

39
-continued
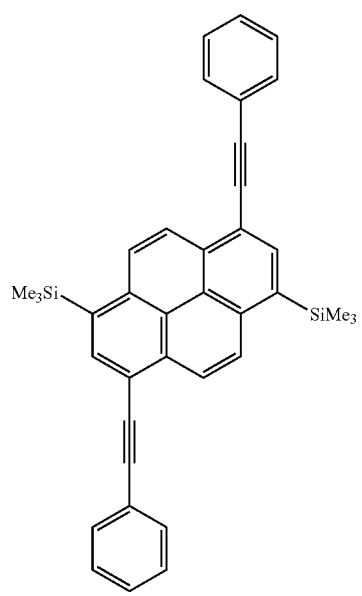
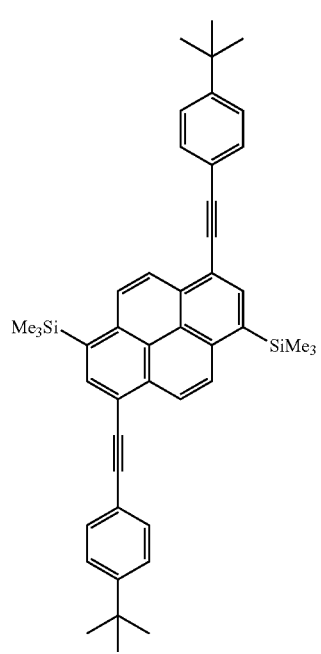
40
-continued
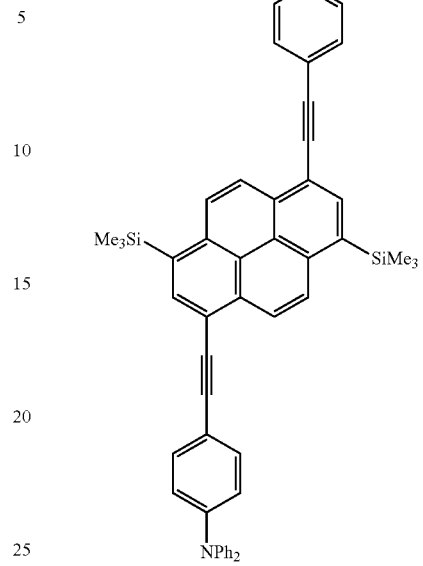
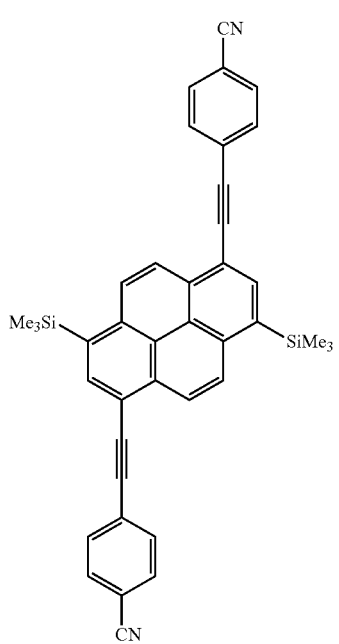

41
-continued
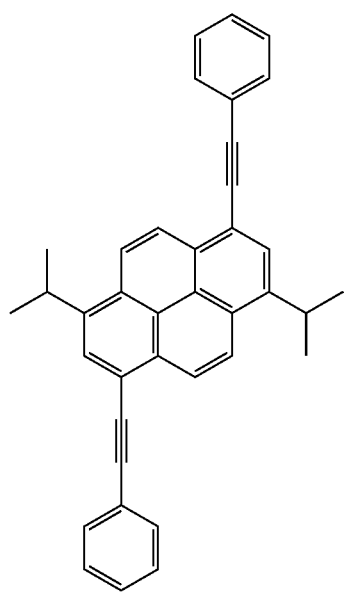
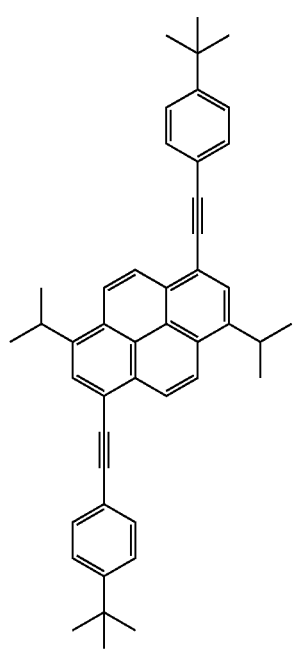
42
-continued
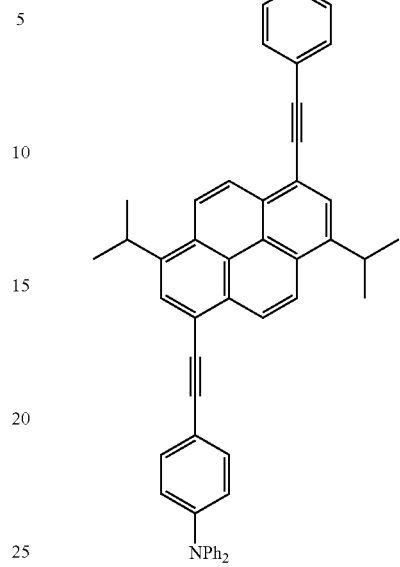
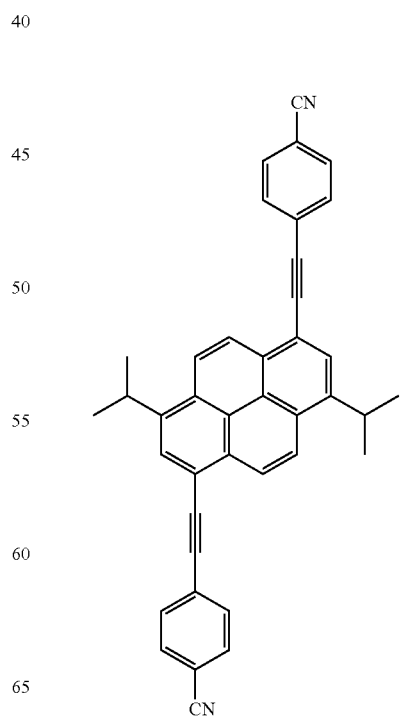

43
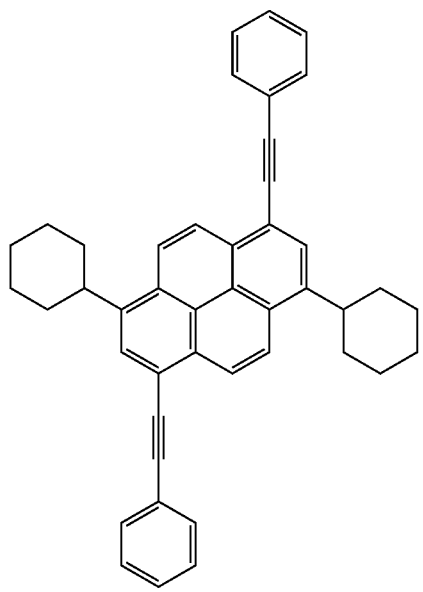
44
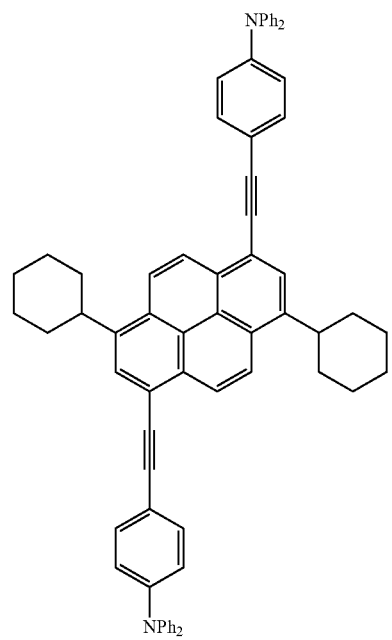
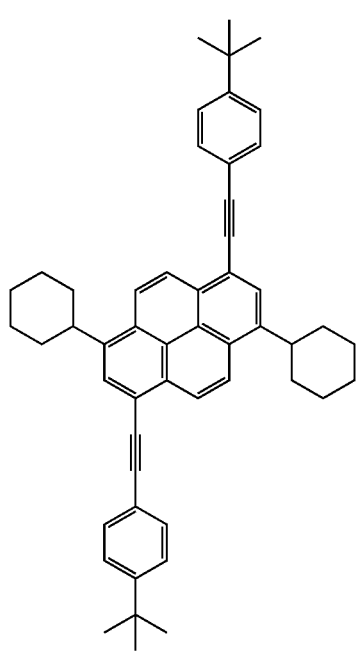
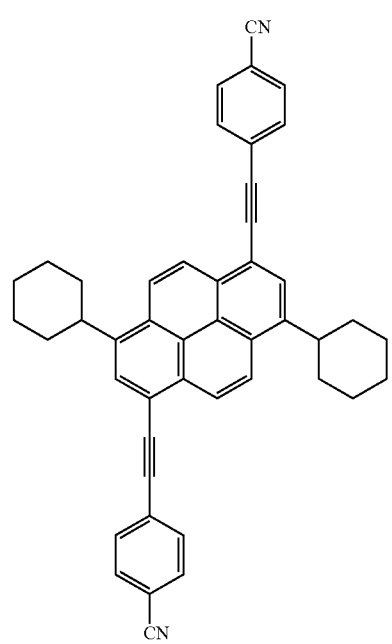

45
-continued
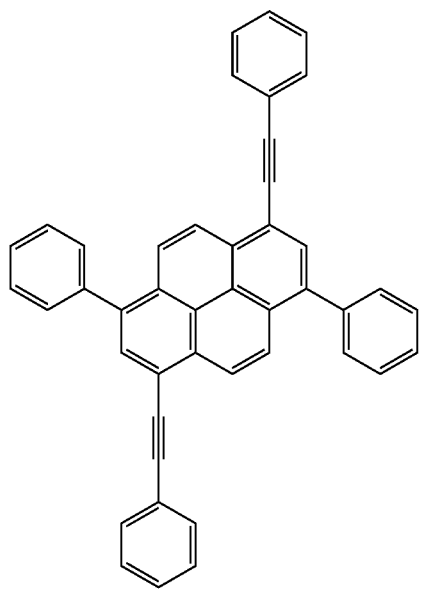
46
-continued
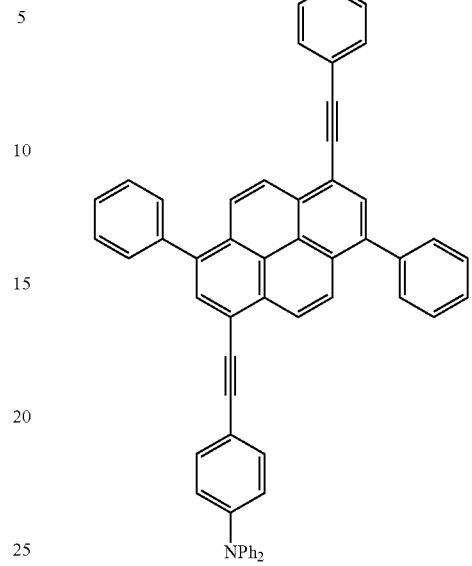
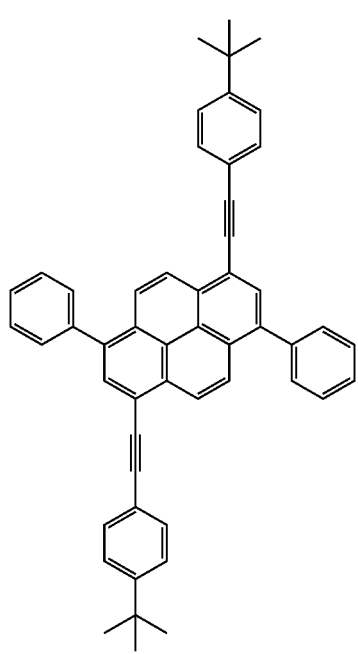
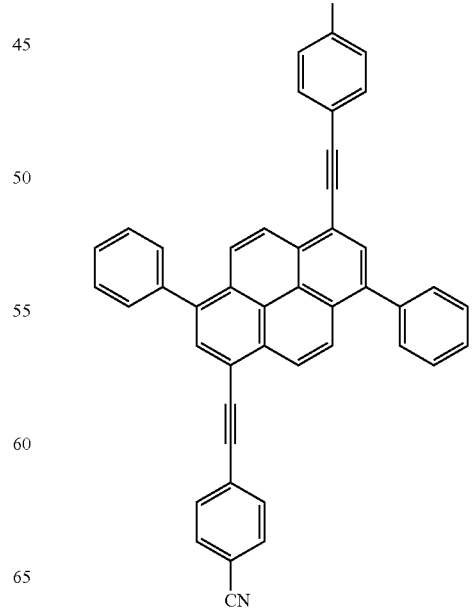

47
-continued
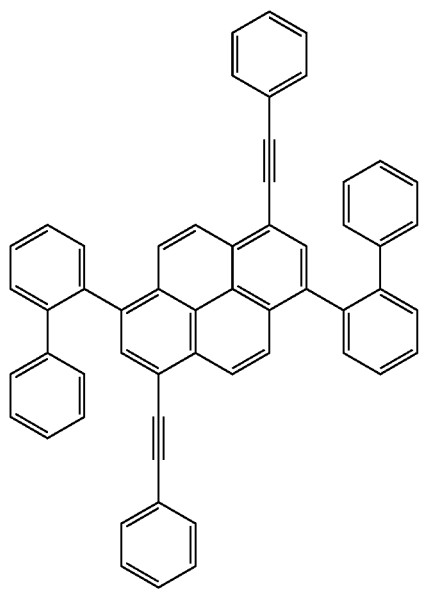
48
-continued
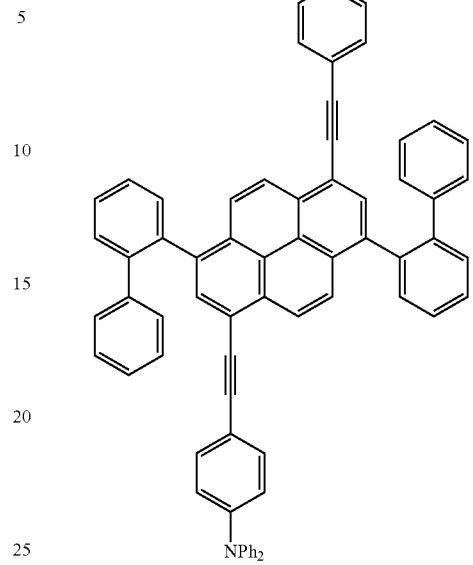
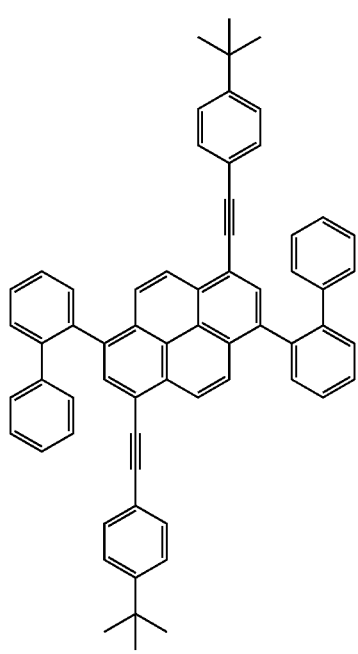
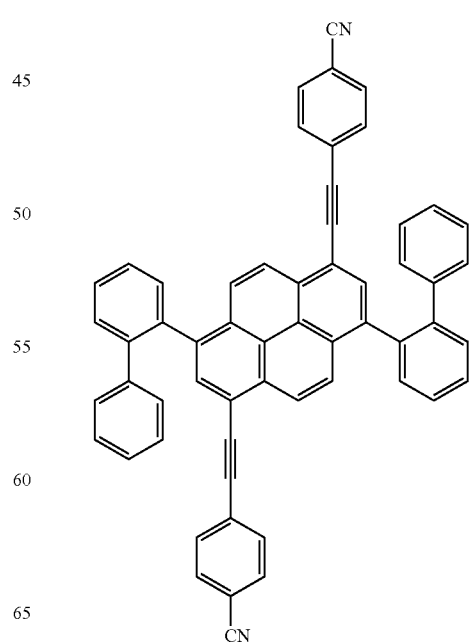

49
-continued
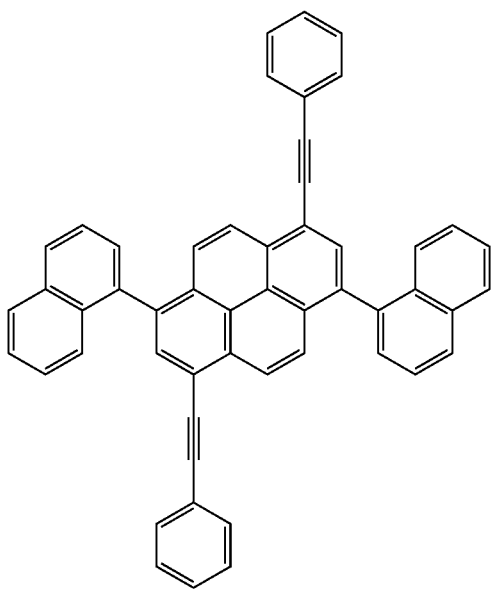
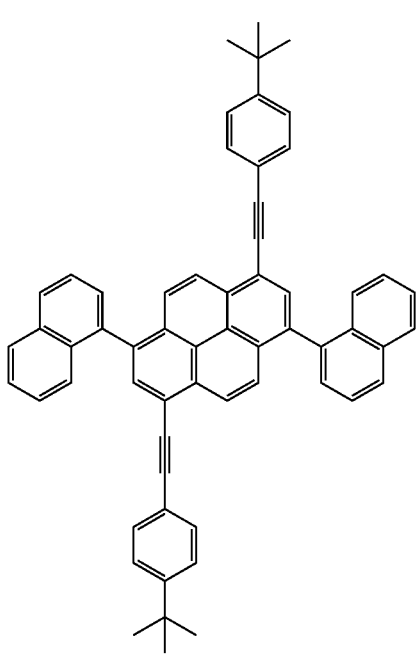
50
-continued
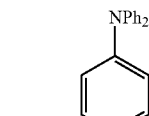
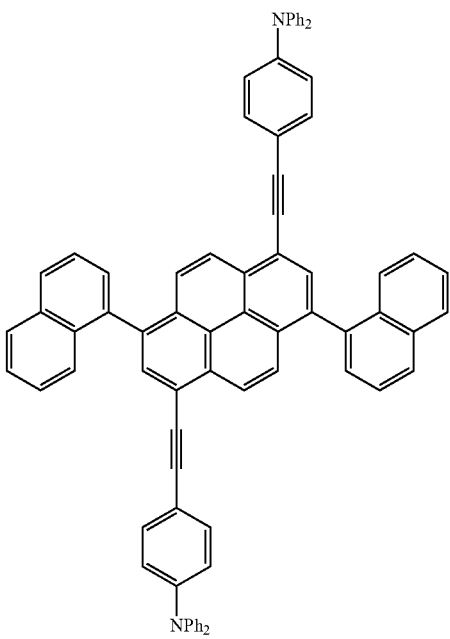
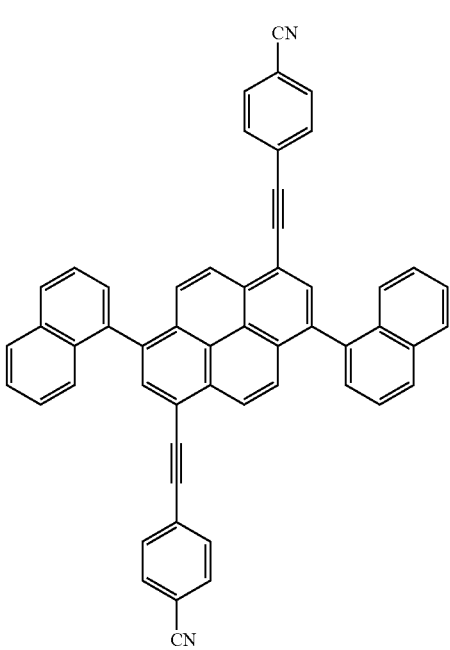

51
-continued
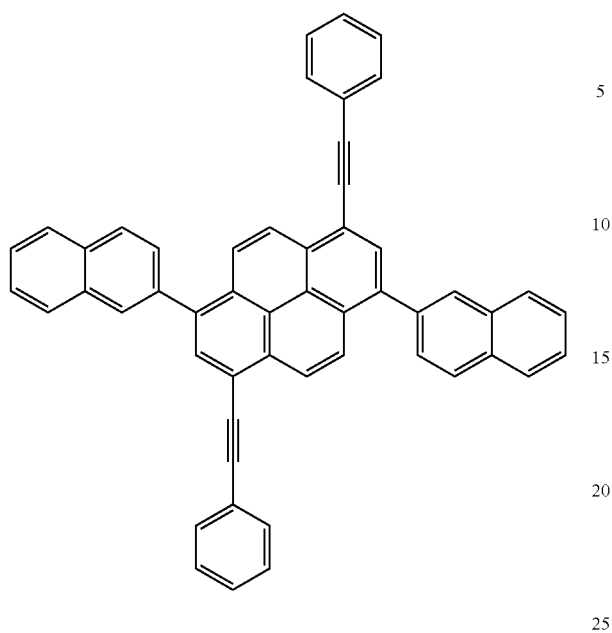
52
-continued
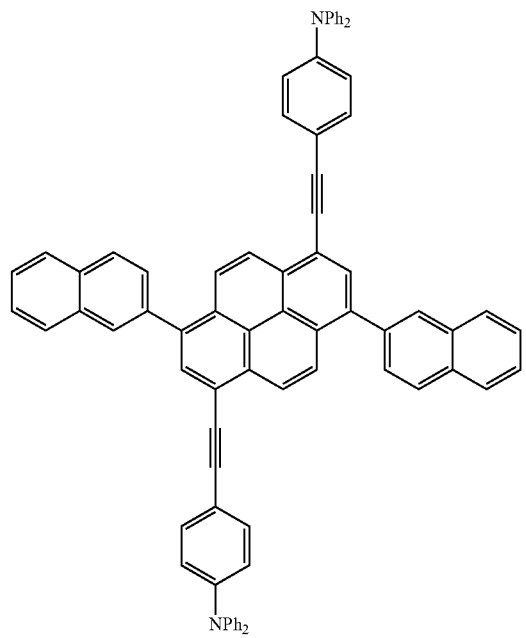
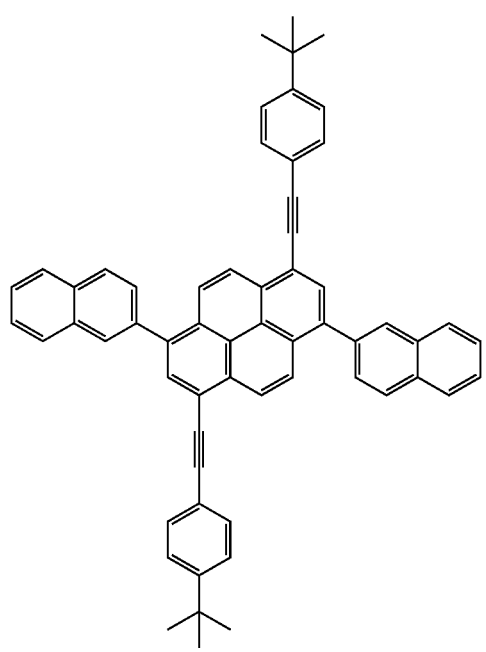
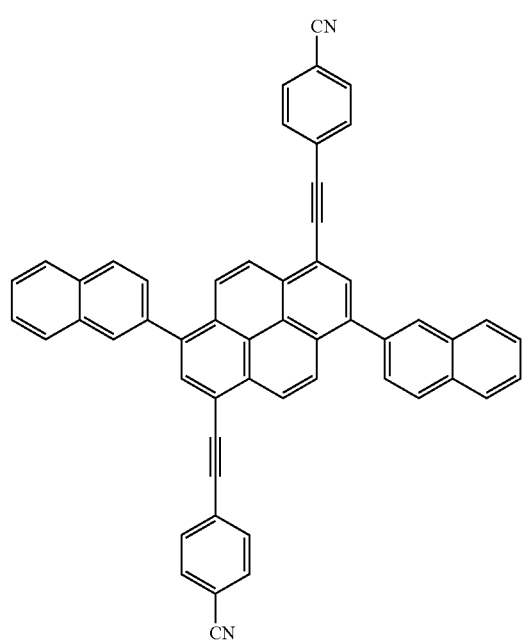

53
-continued
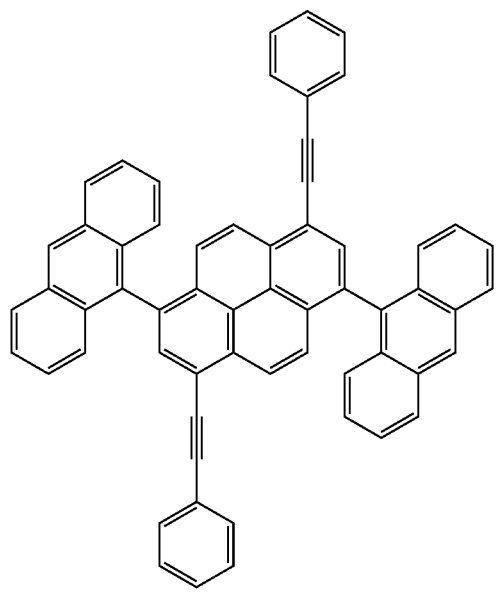
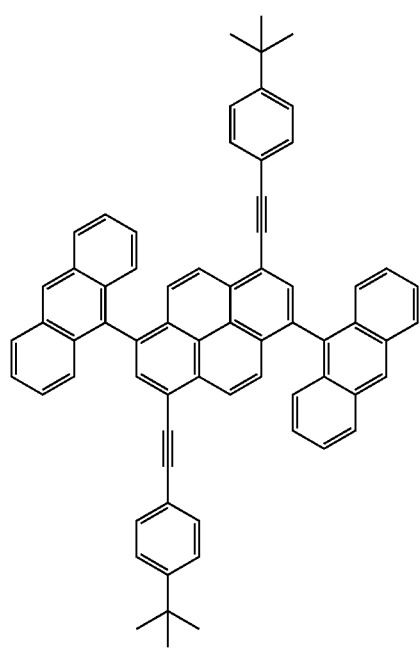
54
-continued
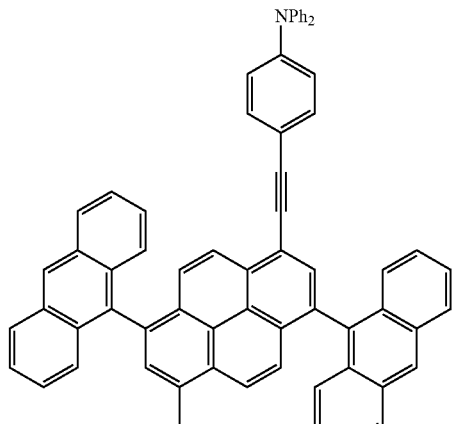
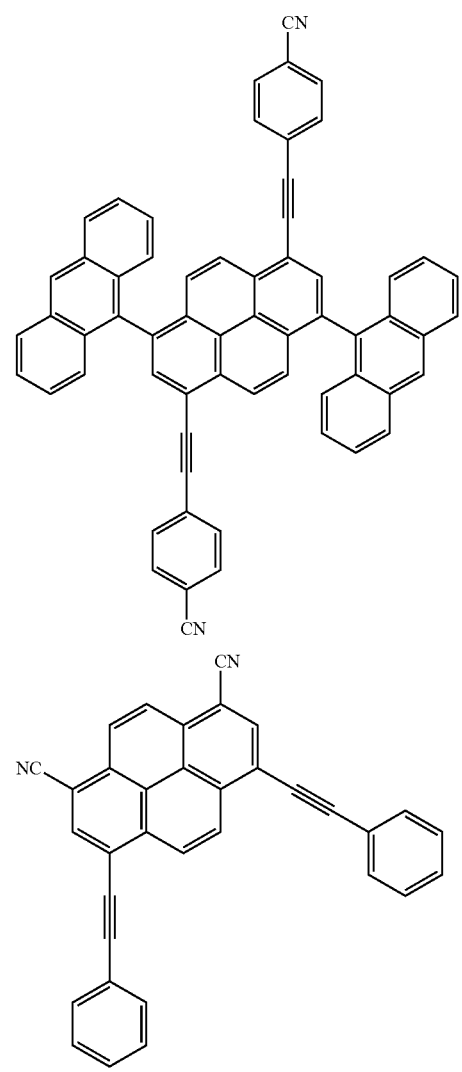

55
-continued
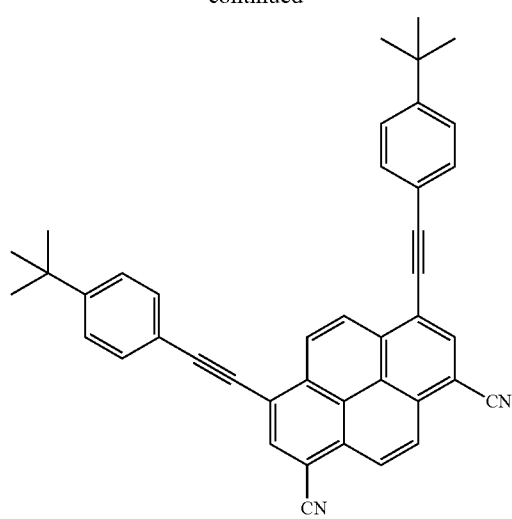
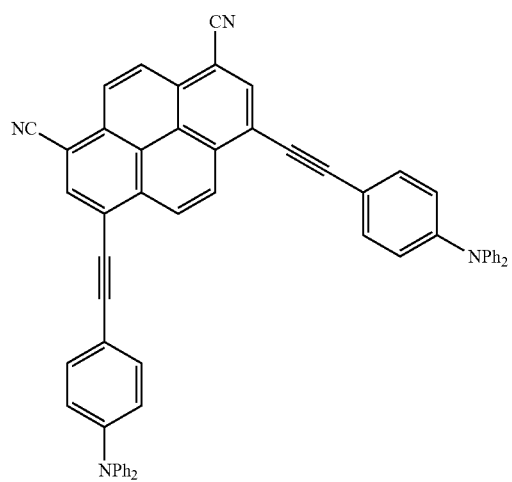
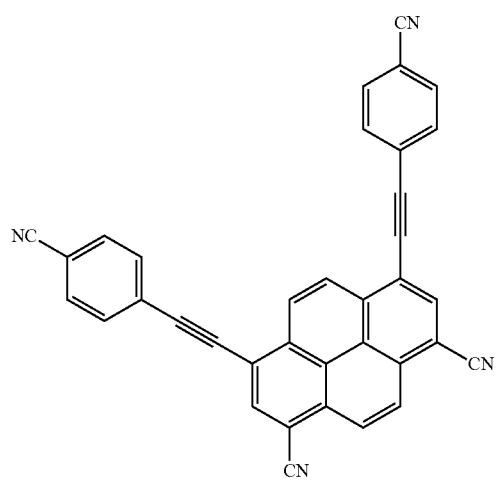
56
-continued
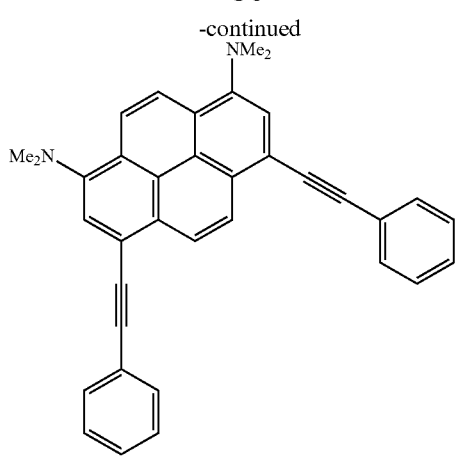
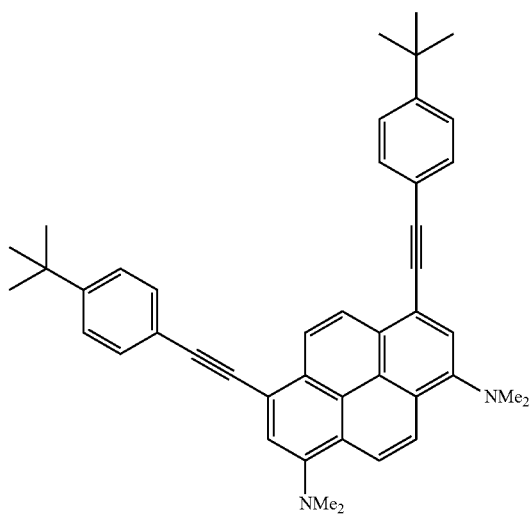
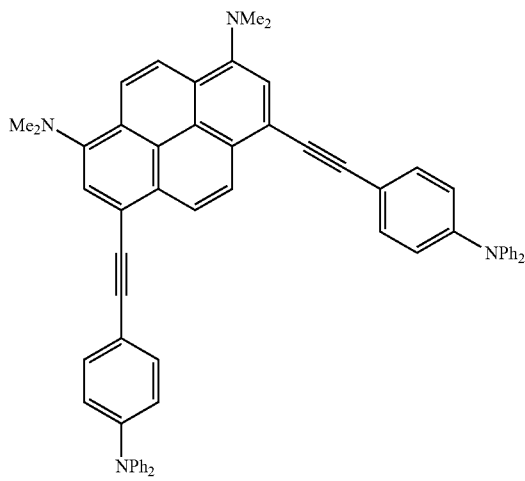

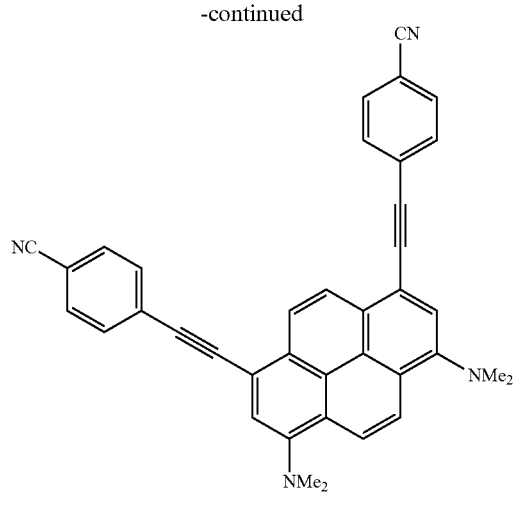
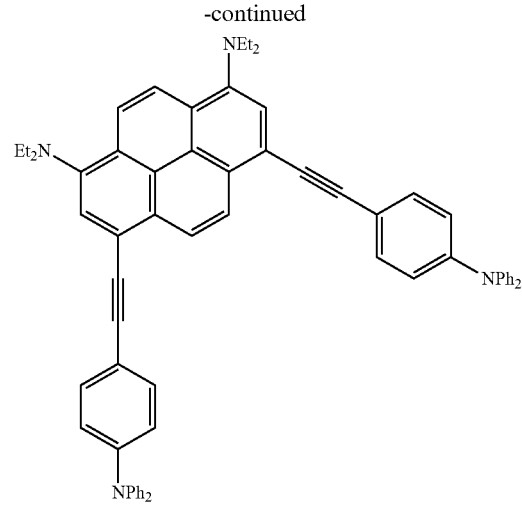
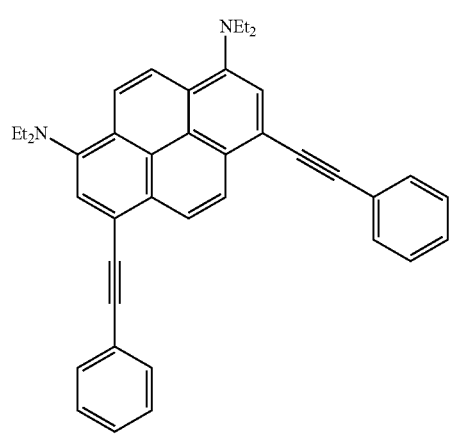
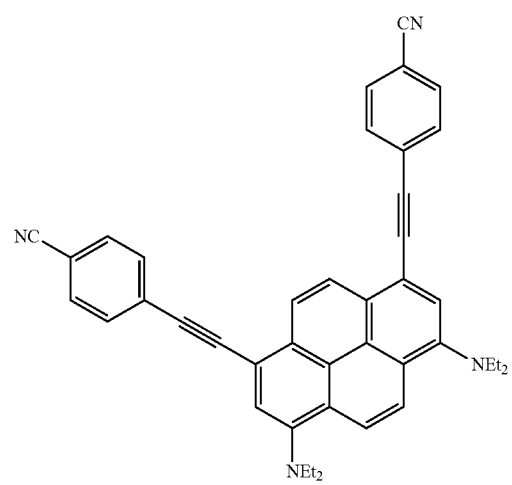
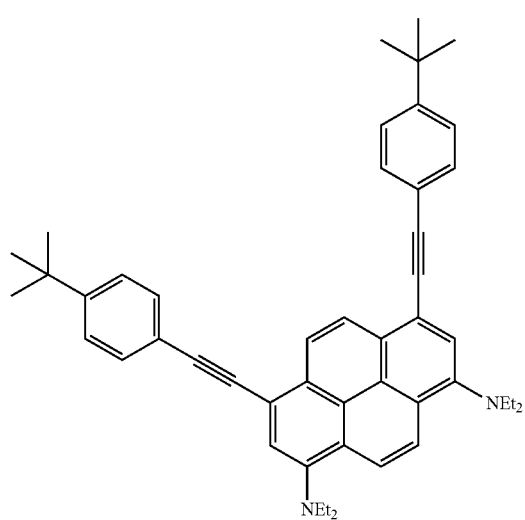
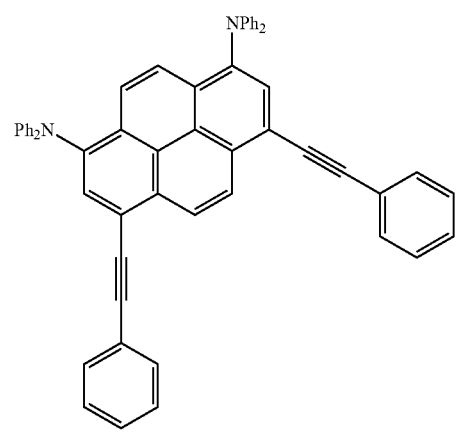

-continued
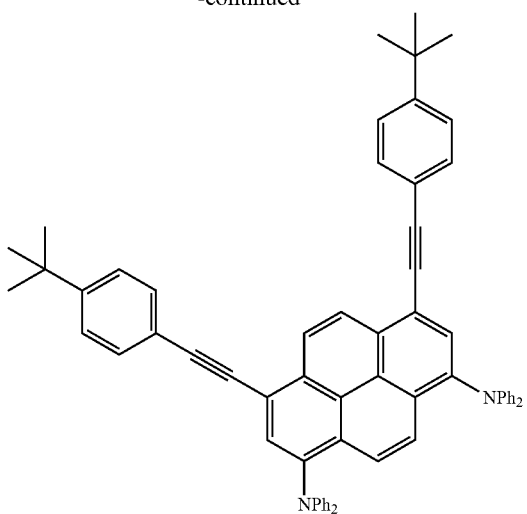
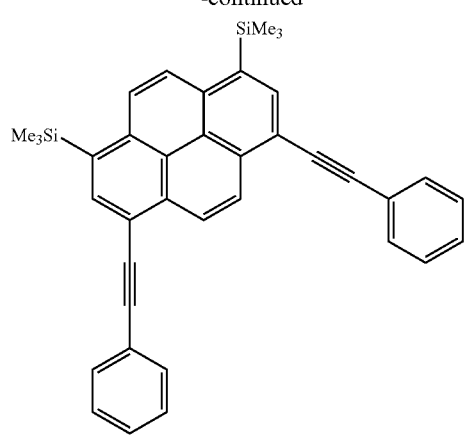
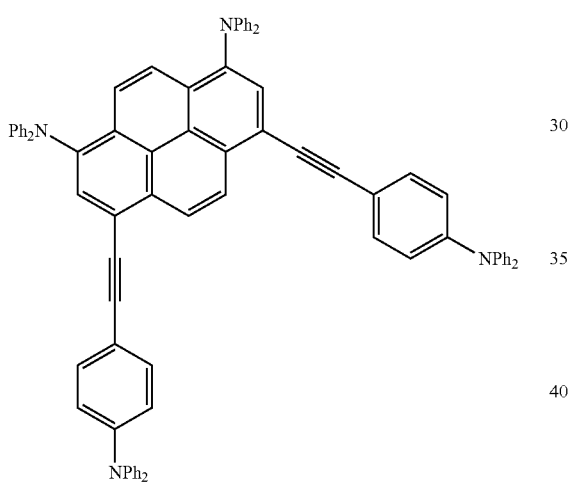
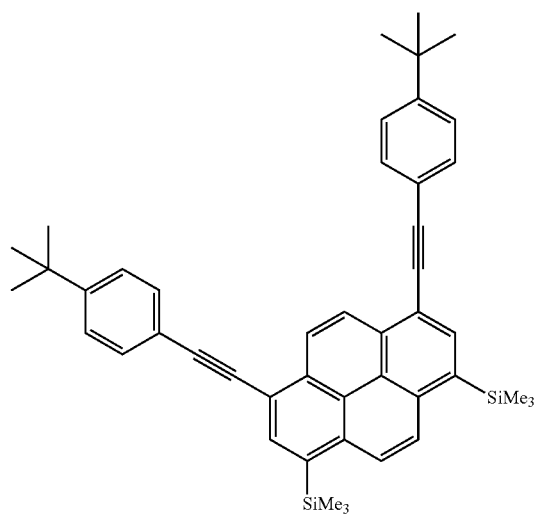
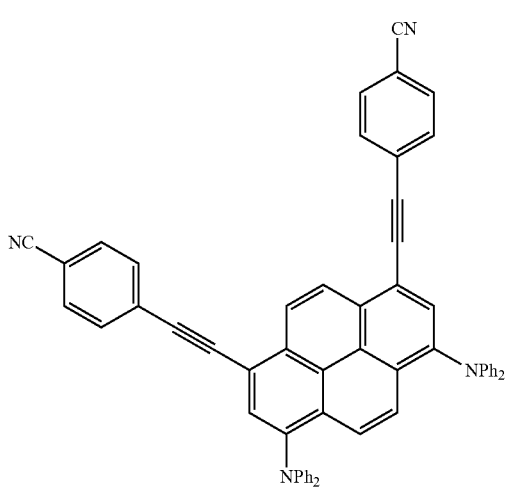
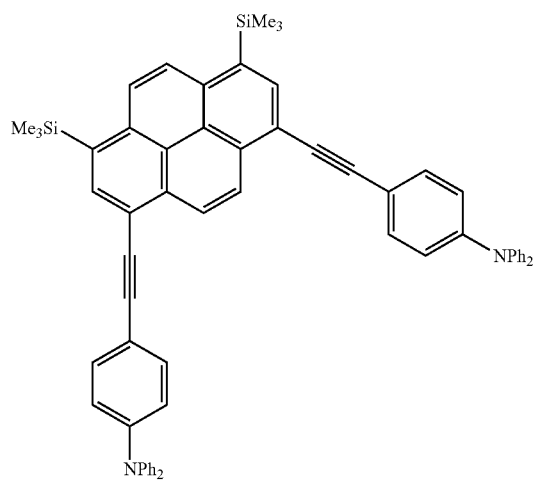

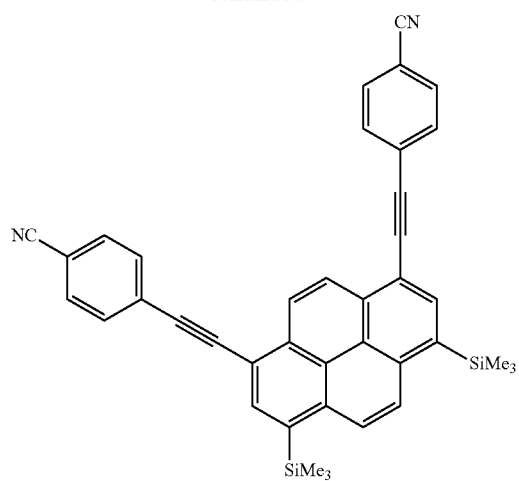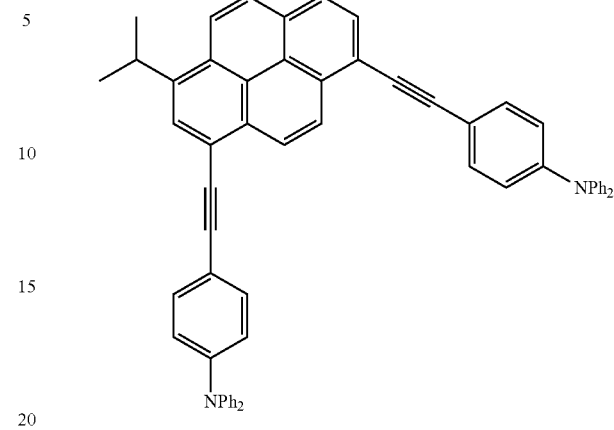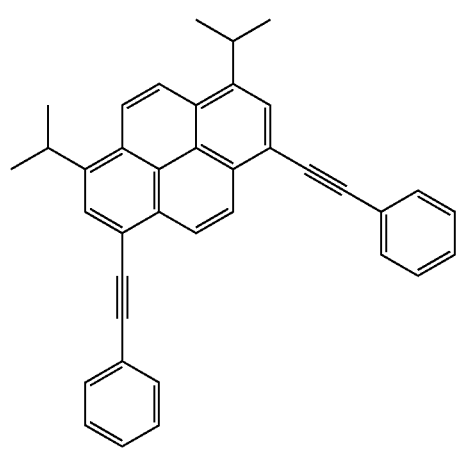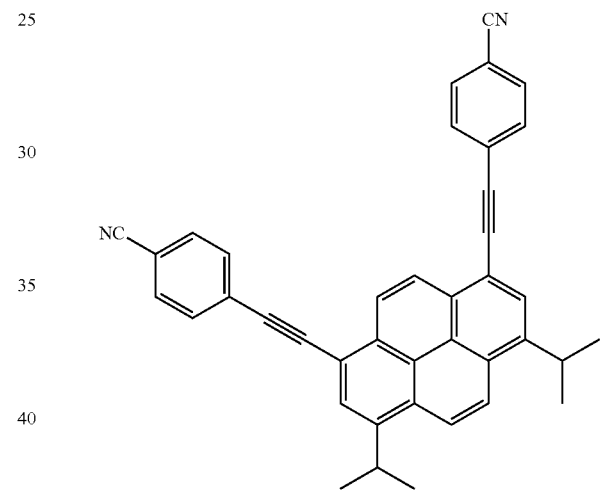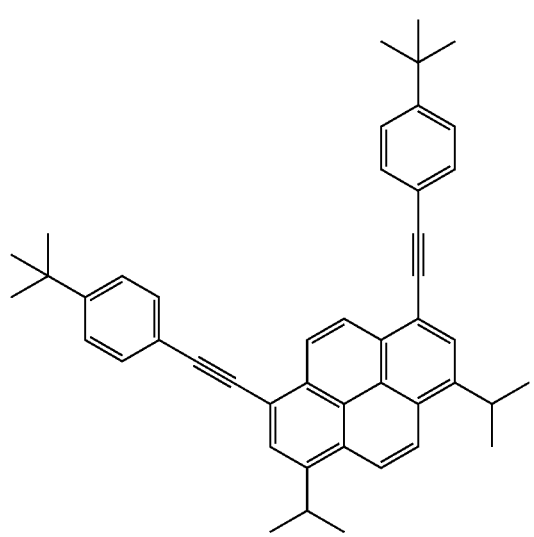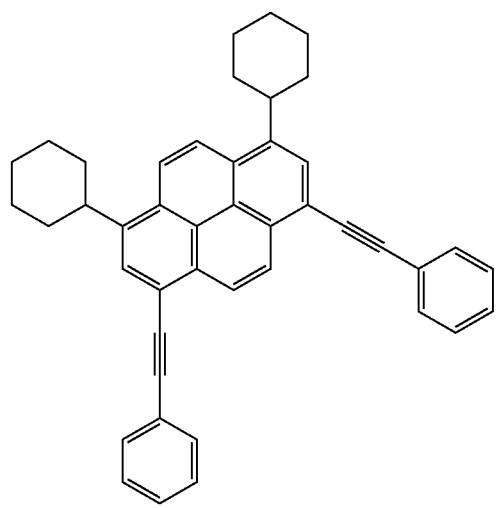

63
-continued
64
-continued
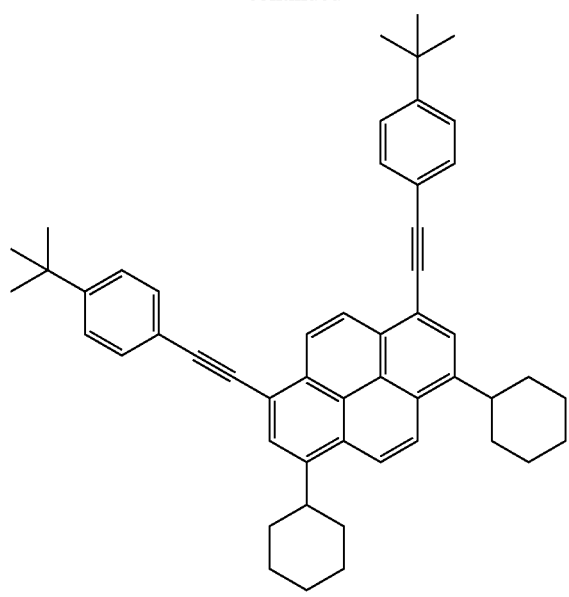
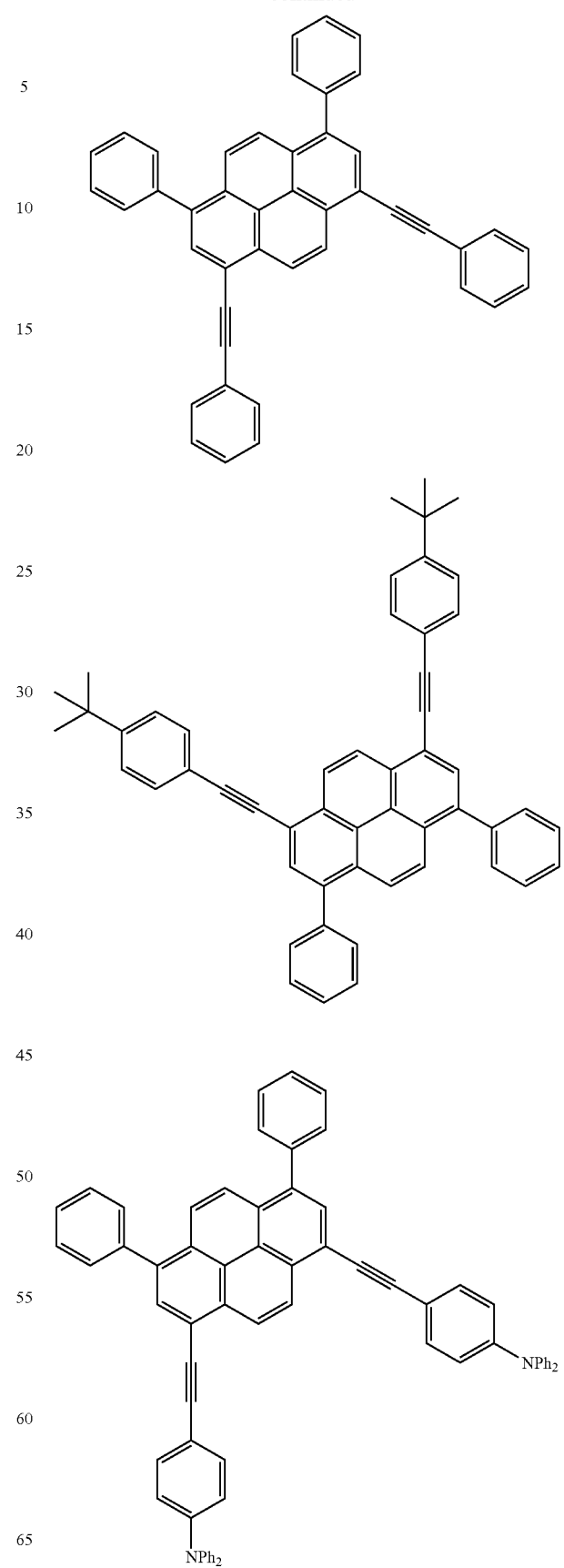

65
-continued
66
-continued
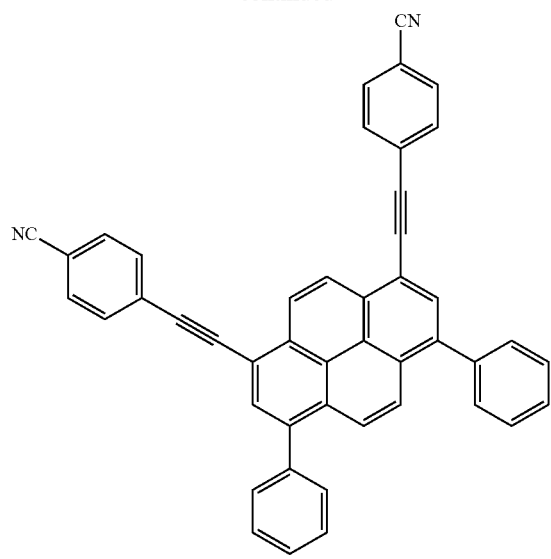
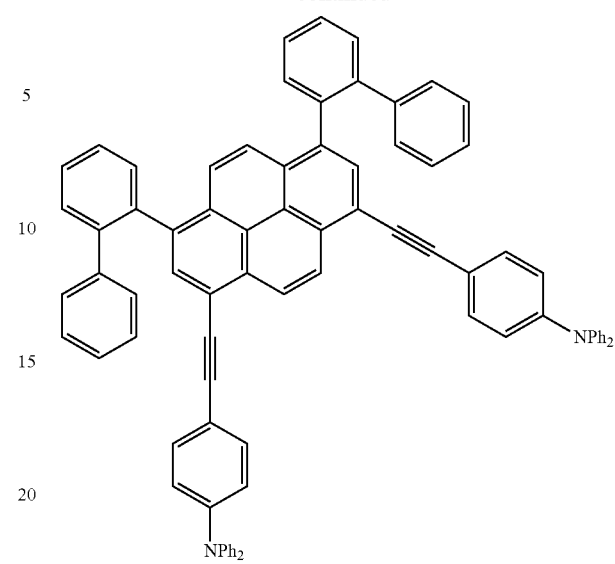
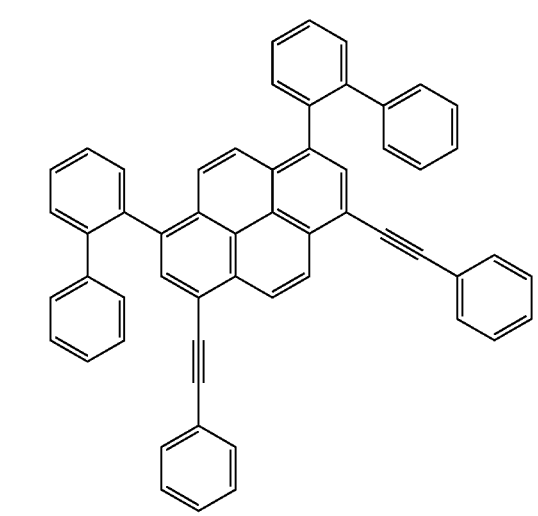
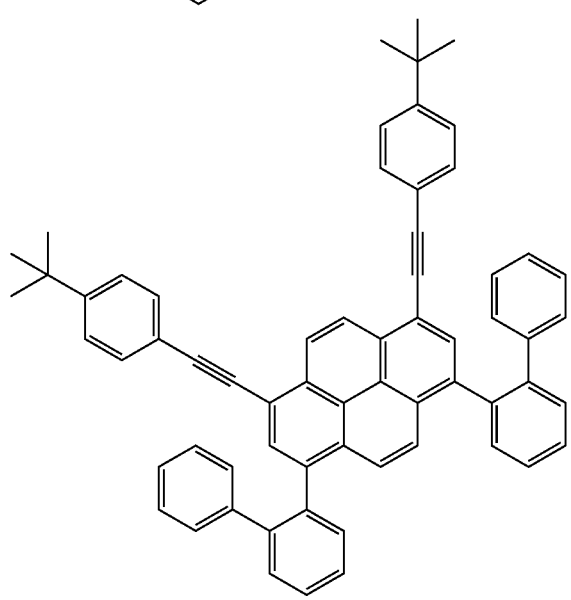
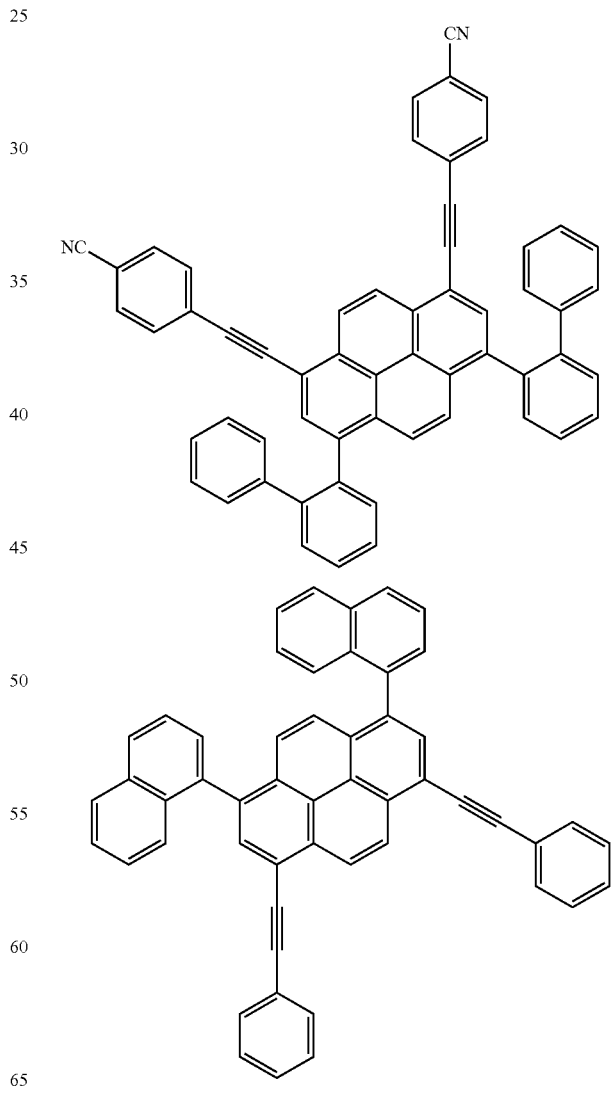

67
-continued
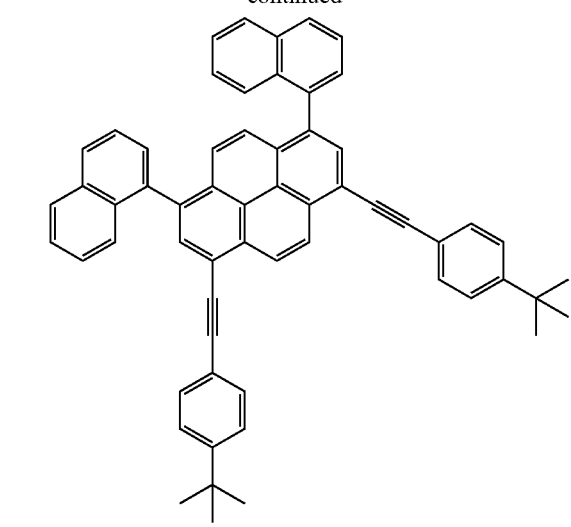
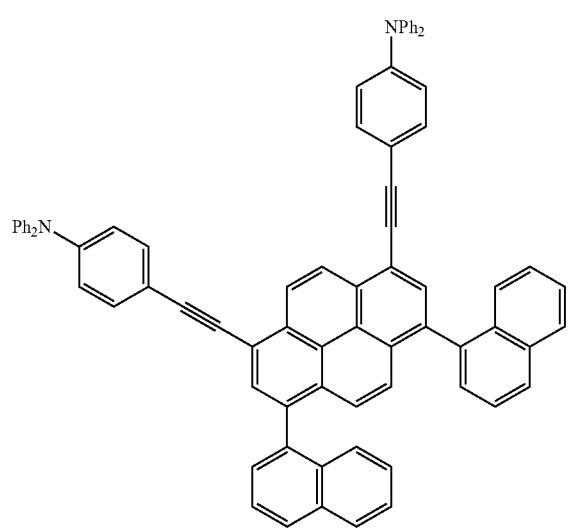
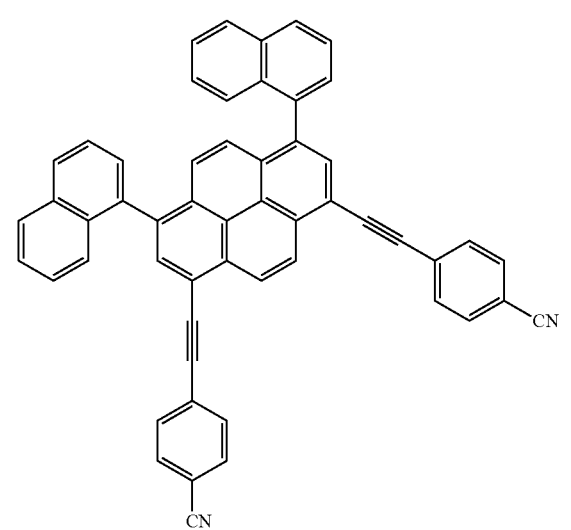
68
-continued
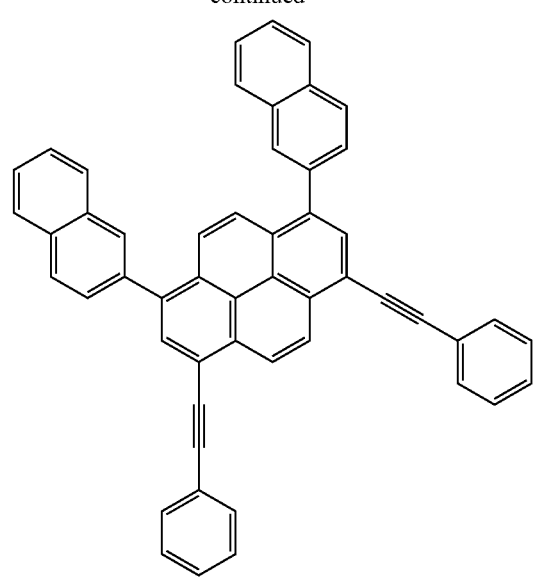
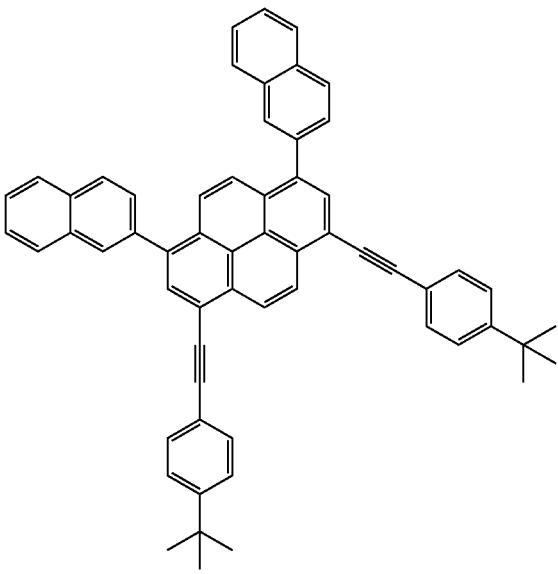
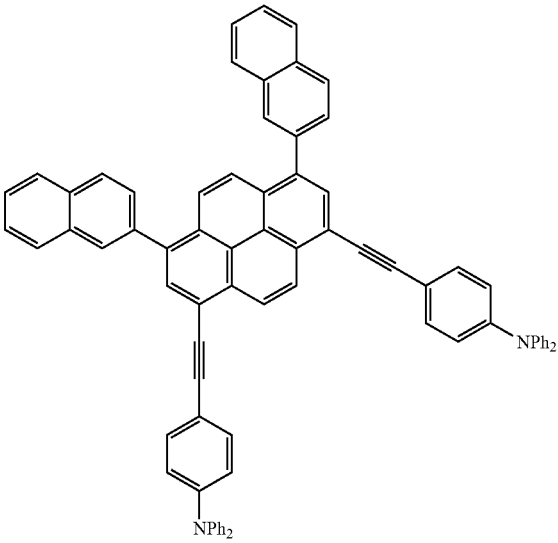

-continued

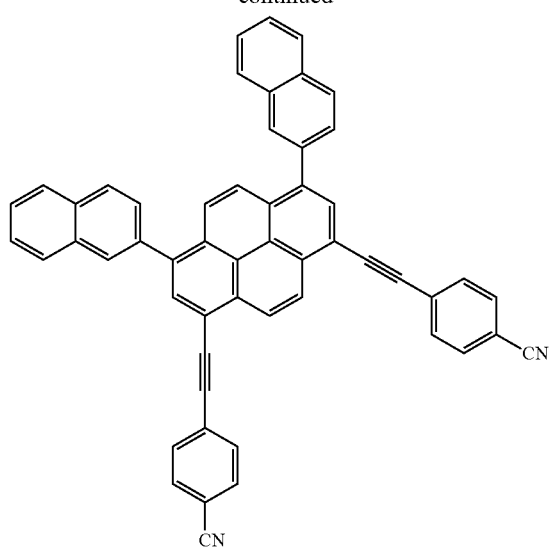

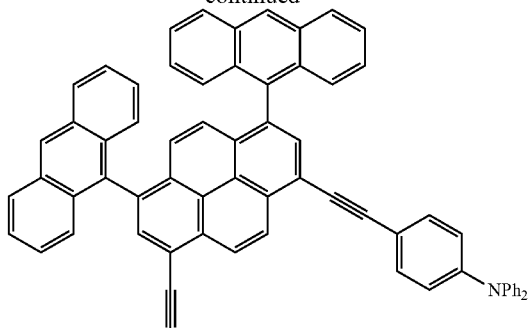

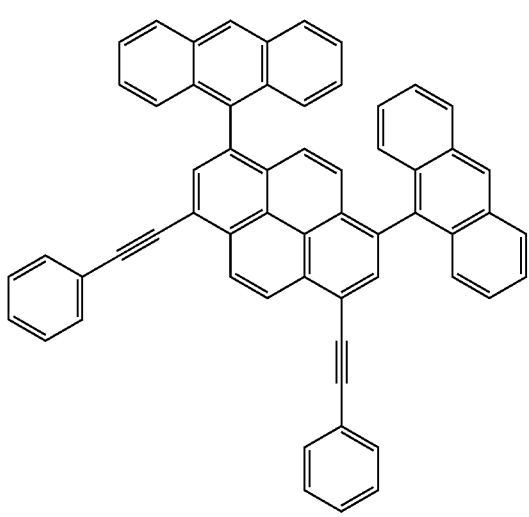

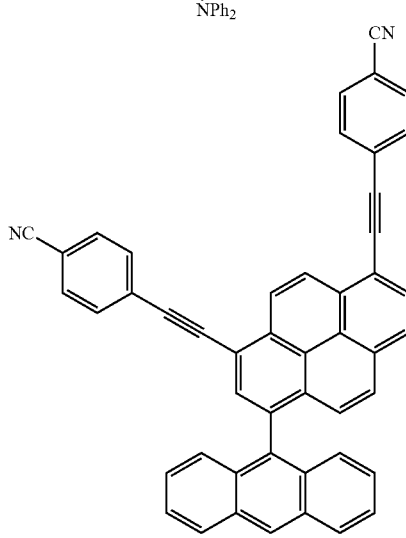

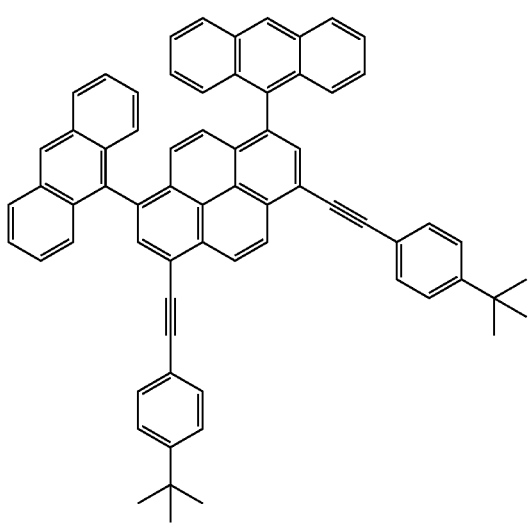

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An optoelectronic device comprising a light-emitting layer which comprises an organic molecule, the organic molecule comprising a structure of formula I:

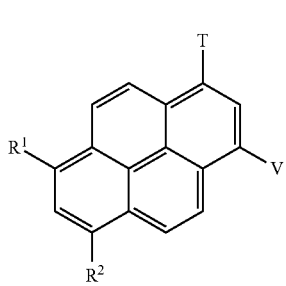

Formula I wherein

T and V is independently from another selected from the group consisting of $R^1$ and $R^2$;

$R^1$ is at each occurrence comprising or consisting of a structure of formula II:

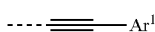

Formula II which is bonded via the position marked by the dotted line;

$Ar^1$ is $C_6$-$C_{60}$-aryl, which is optionally substituted with one or more substituents $R^6$;

$R^2$ is at each occurrence independently from another selected from the group consisting of OPh, SPh, $CF_3$, CN, F, $Si(C_1$-$C_5$-alkyl)$_3$, $Si(Ph)_3$, $C_1$-$C_5$-alkyl,
wherein optionally one or more hydrogen atoms are independently from each other substituted by deuterium, CN, $CF_3$, or F;

$C_1$-$C_5$-alkoxy,
wherein optionally one or more hydrogen atoms are independently from each other substituted by deuterium, CN, $CF_3$, or F;

$C_1$-$C_5$-thioalkoxy,
wherein optionally one or more hydrogen atoms are independently from each other substituted by deuterium, CN, $CF_3$, or F;

$C_2$-$C_5$-alkenyl,
wherein optionally one or more hydrogen atoms are independently from each other substituted by deuterium, CN, $CF_3$, or F;

$C_2$-$C_5$-alkynyl,
wherein optionally one or more hydrogen atoms are independently from each other substituted by deuterium, CN, $CF_3$, or F;

$C_6$-$C_{18}$-aryl,
which is optionally substituted with one or more $C_1$-$C_5$-alkyl substituents:

$C_3$-$C_{17}$-heteroaryl,
which is optionally substituted with one or more $C_1$-$C_5$-alkyl substituents;

$N(C_6$-$C_{18}$-aryl)$_2$,
$N(C_3$-$C_{17}$-heteroaryl)$_2$, and
$N(C_3$-$C_{17}$-heteroaryl) ($C_6$-$C_{18}$-aryl); and $R^6$ is at each occurrence independently from another selected from the group consisting of hydrogen, deuterium, OPh, SPh, $CF_3$, CN, F, $Si(C_1$-$C_5$-alkyl)$_3$, $Si(Ph)_3$, $C_1$-$C_5$-alkyl,
wherein optionally one or more hydrogen atoms are independently from each other substituted by deuterium, CN, $CF_3$, or F;

$C_1$-$C_5$-alkoxy,
wherein optionally one or more hydrogen atoms are independently from each other substituted by deuterium, CN, $CF_3$, or F;

$C_1$-$C_5$-thioalkoxy,
wherein optionally one or more hydrogen atoms are independently from each other substituted by deuterium, CN, $CF_3$, or F;

$C_2$-$C_5$-alkenyl,
wherein optionally one or more hydrogen atoms are independently from each other substituted by deuterium, CN, $CF_3$, or F;

$C_2$-$C_5$-alkynyl,
wherein optionally one or more hydrogen atoms are independently from each other substituted by deuterium, CN, $CF_3$, or F;

$C_6$-$C_{18}$-aryl,
which is optionally substituted with one or more $C_1$-$C_5$-alkyl substituents;

$C_3$-$C_{17}$-heteroaryl,
which is optionally substituted with one or more $C_1$-$C_5$-alkyl substituents;

$N(C_6$-$C_{18}$-aryl)$_2$,
$N(C_3$-$C_{17}$-heteroaryl)$_2$; and
$N(C_3$-$C_{17}$-heteroaryl) ($C_6$-$C_{18}$-aryl); and wherein exactly one moiety selected from the group consisting of T and V is $R^1$ and exactly one moiety selected from the group consisting of T and V is $R^2$, and wherein the light-emitting layer comprises the organic molecule and a host, a first excited triplet state of the host is energetically higher than a first excited triplet state of the organic molecule, a first excited singlet state of the host is energetically higher than a first excited singlet state of the organic molecule, and the organic molecule is configured to receive energy from the host and emit light having an emission maxima of 380 nm to 470 nm.

2. The optoelectronic device according to claim 1, wherein $Ar^1$ is selected from the group consisting of:

Ph, which is optionally substituted with one or more substituents independently from each other selected from the group consisting of Me, $^i$Pr, $^t$Bu, CN, $CF_3$, and Ph, naphthyl, which is optionally substituted with one or more substituents independently from each other selected from the group consisting of Me, $^i$Pr, $^t$Bu, CN, $CF_3$, and Ph, and anthracenyl, which is optionally substituted with one or more substituents independently from each other selected from the group consisting of Me, $^i$Pr, $^t$Bu, CN, $CF_3$, and Ph.

3. The optoelectronic device according to claim 1, wherein $R^1$ is selected from the group consisting of:

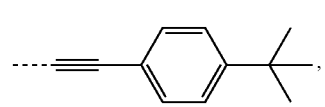

Formula IIb

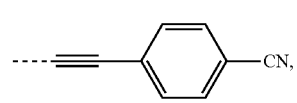

Formula IIc

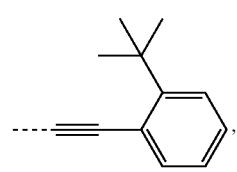

Formula IId

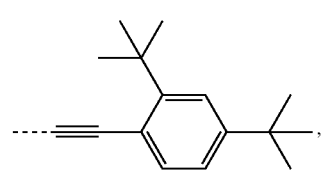

Formula IIe

4. The optoelectronic device according to claim 1, wherein $R^1$ is selected from the group consisting of:

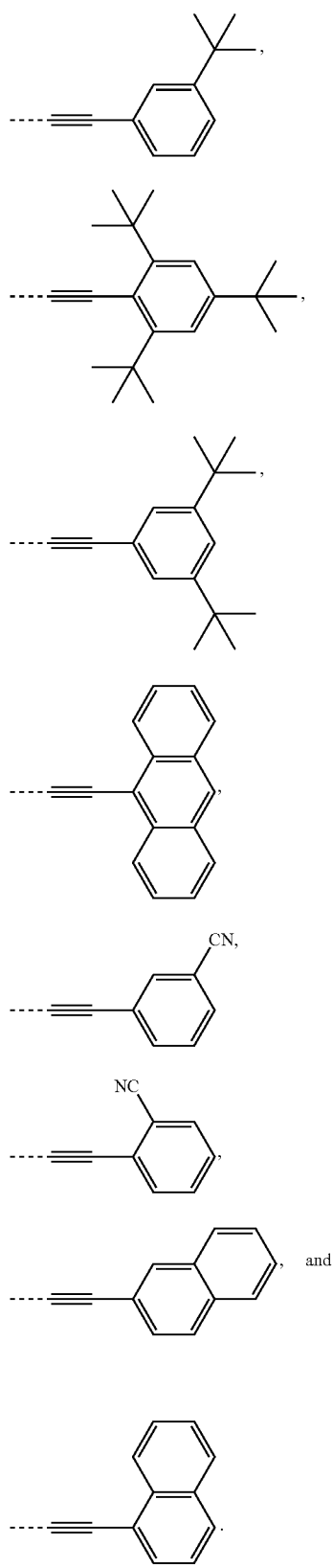

Formula IIf

Formula IIg

Formula IIh

Formula IIi

Formula IIj

Formula IIk

Formula IIm

Formula IIn

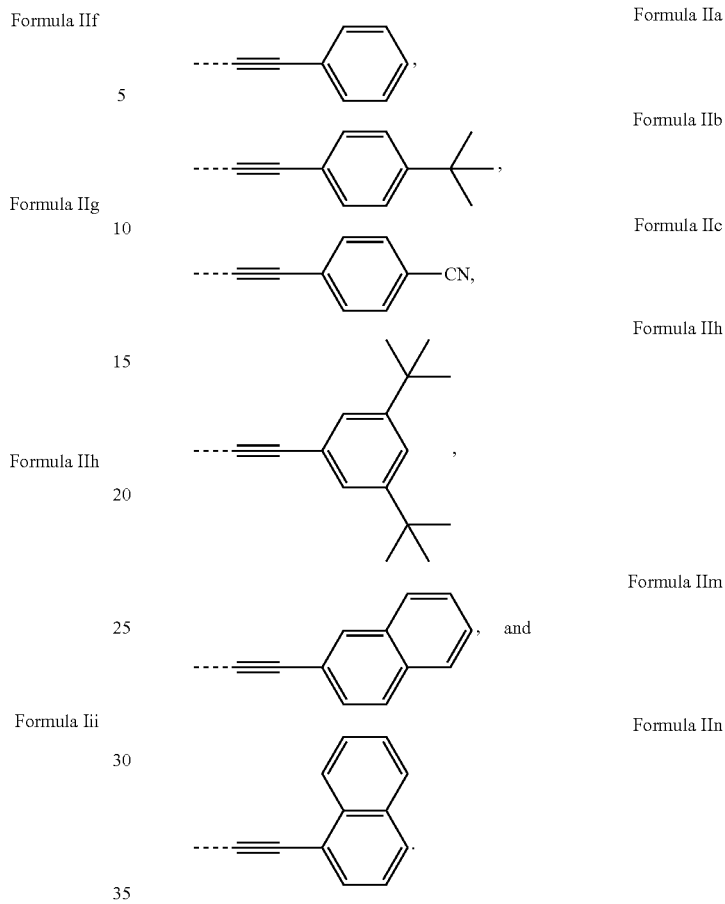

Formula IIa

Formula IIb

Formula IIc

Formula IIh

Formula IIm

Formula IIn

5. An optoelectronic device comprising a light-emitting layer which comprises an organic molecule, the organic molecule comprising a structure of formula I:

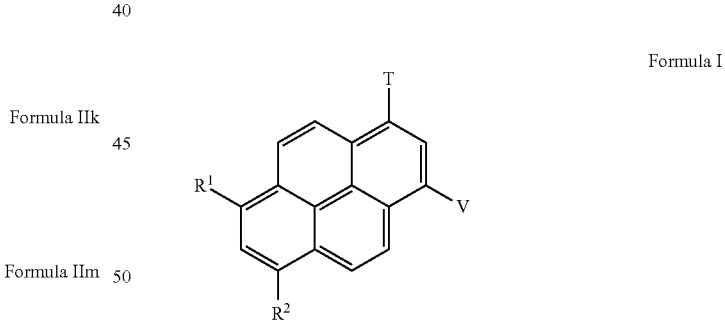

Formula I wherein
T and V is independently from another selected from the group consisting of $R^1$ and $R^2$;
$R^1$ is at each occurrence comprising or consisting of a structure of formula II:

----≡—Ar¹

Formula II which is bonded via the position marked by the dotted line;
Ar¹ is $C_6$-$C_{60}$-aryl, which is optionally substituted with one or more substituents $R^6$:

$R^2$ is selected from the group consisting of:

Me, $^i$Pr, $^t$Bu, SiMe$_3$, SiPh$_3$, and

Ph, which is optionally substituted with one or more substituents independently from each other selected from the group consisting of Me, $^i$Pr, $^t$Bu, and Ph;

$R^6$ is at each occurrence independently from another selected from the group consisting of hydrogen, deuterium, OPh, SPh, CF$_3$, CN, F, Si(C$_1$-C$_5$-alkyl)$_3$, Si(Ph)$_3$, C$_1$-C$_5$-alkyl,
wherein optionally one or more hydrogen atoms are independently from each other substituted by deuterium, CN, CF$_3$, or F;

C$_1$-C$_5$-alkoxy,
wherein optionally one or more hydrogen atoms are independently from each other substituted by deuterium, CN, CF$_3$, or F;

C$_1$-C$_5$-thioalkoxy,
wherein optionally one or more hydrogen atoms are independently from each other substituted by deuterium, CN, CF$_3$, or F;

C$_2$-C$_5$-alkenyl,
wherein optionally one or more hydrogen atoms are independently from each other substituted by deuterium, CN, CF$_3$, or F:

C$_2$-C$_5$-alkynyl,
wherein optionally one or more hydrogen atoms are independently from each other substituted by deuterium, CN, CF$_3$, or F:

C$_6$-C$_{18}$-aryl,
which is optionally substituted with one or more C$_1$-C$_5$-alkyl substituents;

C$_3$-C$_{17}$-heteroaryl,
which is optionally substituted with one or more C$_1$-C$_5$-alkyl substituents:

N(C$_6$-C$_{18}$-aryl)$_2$,

N(C$_3$-C$_{17}$-heteroaryl)$_2$, and

N(C$_3$-C$_{17}$-heteroaryl) (C$_6$-C$_{18}$-aryl);

wherein exactly one moiety selected from the group consisting of T and V is $R^1$ and exactly one moiety selected from the consisting of T and V is $R^2$, and wherein the light-emitting layer comprises the organic molecule and a host, a first excited triplet state of the host is energetically higher than a first excited triplet state of the organic molecule, a first excited singlet state of the host is energetically higher than a first excited singlet state of the organic molecule, and the organic molecule is configured to receive energy from the host and emit light having an emission maxima of 380 nm to 470 nm.

6. The optoelectronic device according to claim 5, wherein $R^2$ is selected from the group consisting of:

$^i$Pr, and

Ph, which is optionally substituted with one or more Ph substituents.

7. The optoelectronic device according to claim 1, wherein the organic molecule comprises a structure of formula IIIa:

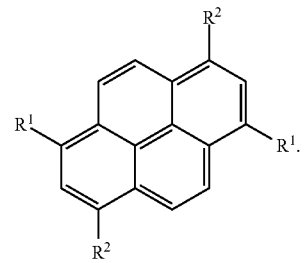

Formula IIIa

8. The optoelectronic device according to claim 1, wherein the organic molecule comprises a structure of formula IIIb:

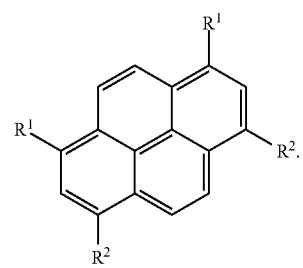

Formula IIIb

9. A composition comprising:
(a) at least one organic molecule comprising a structure of formula I as an emitter:

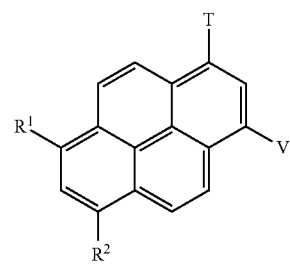

Formula I wherein
T and V is independently from another selected from the group consisting of $R^1$ and $R^2$;
$R^1$ is at each occurrence comprising or consisting of a structure of formula II:

Formula II which is bonded via the position marked by the dotted line;

Ar$^1$ is C$_6$-C$_{60}$-aryl, which is optionally substituted with one or more substituents $R^6$;

$R^2$ is at each occurrence independently from another selected from the group consisting of OPh, SPh, CF$_3$, CN, F, Si(C$_1$-C$_5$-alkyl)$_3$, Si(Ph)$_3$, C$_1$-C$_5$-alkyl,
wherein optionally one or more hydrogen atoms are independently from each other substituted by deuterium, CN, CF$_3$, or F;

$C_1$-$C_5$-alkoxy,
  wherein optionally one or more hydrogen atoms are independently from each other substituted by deuterium, CN, $CF_3$, or F;
$C_1$-$C_5$-thioalkoxy,
  wherein optionally one or more hydrogen atoms are independently from each other substituted by deuterium, CN, $CF_3$, or F;
$C_2$-$C_5$-alkenyl,
  wherein optionally one or more hydrogen atoms are independently from each other substituted by deuterium, CN, $CF_3$, or F;
$C_2$-$C_5$-alkynyl,
  wherein optionally one or more hydrogen atoms are independently from each other substituted by deuterium, CN, $CF_3$, or F;
$C_6$-$C_{18}$-aryl,
  which is optionally substituted with one or more $C_1$-$C_5$-alkyl substituents;
$C_3$-$C_{17}$-heteroaryl,
  which is optionally substituted with one or more $C_1$-$C_5$-alkyl substituents;
$N(C_6$-$C_{18}$-aryl$)_2$,
$N(C_3$-$C_{17}$-heteroaryl$)_2$, and
$N(C_3$-$C_{17}$-heteroaryl$)$ $(C_6$-$C_{18}$-aryl$)$; and
$R^6$ is at each occurrence independently from another selected from the group consisting of hydrogen, deuterium, OPh, SPh, $CF_3$, CN, F, $Si(C_1$-$C_5$-alkyl$)_3$, $Si(Ph)_3$,
$C_1$-$C_5$-alkyl,
  wherein optionally one or more hydrogen atoms are independently from each other substituted by deuterium, CN, $CF_3$, or F;
$C_1$-$C_5$-alkoxy,
  wherein optionally one or more hydrogen atoms are independently from each other substituted by deuterium, CN, $CF_3$, or F;
$C_1$-$C_5$-thioalkoxy,
  wherein optionally one or more hydrogen atoms are independently from each other substituted by deuterium, CN, $CF_3$, or F;
$C_2$-$C_5$-alkenyl,
  wherein optionally one or more hydrogen atoms are independently from each other substituted by deuterium, CN, $CF_3$, or F;
$C_2$-$C_5$-alkynyl,
  wherein optionally one or more hydrogen atoms are independently from each other substituted by deuterium, CN, $CF_3$, or F;
$C_6$-$C_{18}$-aryl,
  which is optionally substituted with one or more $C_1$-$C_5$-alkyl substituents;
$C_3$-$C_{17}$-heteroaryl,
  which is optionally substituted with one or more $C_1$-$C_5$-alkyl substituents;
$N(C_6$-$C_{18}$-aryl$)_2$,
$N(C_3$-$C_{17}$-heteroaryl$)_2$, and
$N(C_3$-$C_{17}$-heteroaryl$)$ $(C_6$-$C_{18}$-aryl$)$;
wherein exactly one moiety selected from the group consisting of T and V is $R^1$ and exactly one moiety selected from the group consisting of T and V is $R^2$ (b) one or more host materials different from the at least one organic molecule, wherein a first excited triplet state of the one or more host materials is energetically higher than a first excited triplet state of the organic molecule, and a first excited singlet state of the one or more host materials is energetically higher than a first excited singlet state of the organic molecule, and (c) optionally one or more dyes and/or one or more solvents, and
wherein the organic molecule is configured to receive energy from the one or more host materials and emit light having an emission maxima of 380 nm to 470 nm.

10. The optoelectronic device according to claim 1, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

11. The optoelectronic device according to claim 10, comprising:
a substrate;
an anode;
a cathode, wherein the anode or the cathode is applied to the substrate; and
at least one light-emitting layer disposed between the anode and the cathode and which comprises the organic molecule.

12. The optoelectronic device according to claim 1, wherein the organic molecule is one of a luminescent emitter, an electron transport material, a hole injection material or a hole blocking material in the optoelectronic device.

13. The optoelectronic device according to claim 12, wherein the optoelectronic device is an organic light-emitting diode, a light-emitting electrochemical cell, an organic light-emitting sensor, an organic diode, an organic solar cell, an organic transistor, an organic field-effect transistor, an organic laser, or a down-conversion element.

14. The optoelectronic device according to claim 13, comprising:
a substrate;
an anode;
a cathode, wherein the anode or the cathode is applied to the substrate; and
at least one light-emitting layer disposed between the anode and the cathode and which comprises the organic molecule.

15. The optoelectronic device according to claim 2, wherein the organic molecule is one of a luminescent emitter, an electron transport material, a hole injection material or a hole blocking material in the optoelectronic device.

16. The optoelectronic device according to claim 15, wherein the optoelectronic device is an organic light-emitting diode, a light-emitting electrochemical cell, an organic light-emitting sensor, an organic diode, an organic solar cell, an organic transistor, an organic field-effect transistor, an organic laser, or a down-conversion element.

17. An optoelectronic device comprising the composition according to claim 9, wherein the optoelectronic device is an organic light-emitting diode, a light-emitting electrochemical cell, an organic light-emitting sensor, an organic diode, an organic solar cell, an organic transistor, an organic field-effect transistor, an organic laser, or a down-conversion element.

18. The optoelectronic device according to claim 17, comprising:
a substrate;
an anode;
a cathode, wherein the anode or the cathode is applied to the substrate; and at least one light-emitting layer disposed between the anode and the cathode and which comprises the organic molecule.

19. A method for producing the optoelectronic device according to claim 1, comprising processing of the organic molecule by a vacuum evaporation method or from a solution.

20. A method for producing an optoelectronic device, comprising processing of the composition according to claim 9 by a vacuum evaporation method or from a solution.

* * * * *